United States Patent [19]
Robinson et al.

[11] Patent Number: 6,153,609
[45] Date of Patent: Nov. 28, 2000

[54] ARYLSULFONYLAMINO HYDROXAMIC ACID DERIVATIVES

[75] Inventors: Ralph P. Robinson, Gales Ferry; Todd A. Blumenkopf, Old Lyme, both of Conn.

[73] Assignee: Pfizer Inc, New York, N.Y.

[21] Appl. No.: 09/242,504

[22] PCT Filed: Jul. 25, 1997

[86] PCT No.: PCT/IB97/00924

§ 371 Date: Feb. 16, 1999

§ 102(e) Date: Feb. 16, 1999

[87] PCT Pub. No.: WO98/07697

PCT Pub. Date: Feb. 26, 1998

Related U.S. Application Data

[60] Provisional application No. 60/024,675, Aug. 23, 1996.

[51] Int. Cl.[7] .................. A61K 31/18; A61K 31/445; A61K 31/495; C07C 311/29; C07D 211/58
[52] U.S. Cl. ...................... 514/227.5; 514/237.5; 514/255.01; 514/315; 514/330; 514/412; 514/423; 514/539; 514/542; 514/550; 544/58.4; 544/159; 544/386; 544/391; 546/226; 546/245; 548/953; 548/540; 560/13; 560/150
[58] Field of Search ..................... 544/58.4, 159, 544/386, 391; 546/226, 245; 548/953, 540; 560/13, 150; 514/227.5, 237.5, 255, 315, 330, 412, 423, 539, 542, 550, 255.01

[56] References Cited

U.S. PATENT DOCUMENTS

| 5,863,949 | 1/1999 | Robinson et al. | 514/575 |
| 5,994,351 | 11/1999 | Robinson et al. | 514/237.5 |

FOREIGN PATENT DOCUMENTS

| 0 606 046 | 7/1994 | European Pat. Off. |
| 9005719 | 5/1990 | WIPO . |
| 9535276 | 12/1995 | WIPO . |
| WO 95 35275 | 12/1995 | WIPO . |
| WO 96 00214 | 1/1996 | WIPO . |
| WO 96 27583 | 9/1996 | WIPO . |
| 9705865 | 2/1997 | WIPO . |

OTHER PUBLICATIONS

Parker et al., The Development of CGS27023A, A Novel, Potent and Orally Active Matrix Metalloprotease Inhibitor, Poster P73 at the Seventh International Conference of the Inflammation Research Association, Sep. 25–29, 1994.

*Primary Examiner*—Richard L. Raymond
*Attorney, Agent, or Firm*—Peter C. Richardson; Paul H. Ginsburg; Adrian G. Looney

[57] ABSTRACT

A compound of the formula

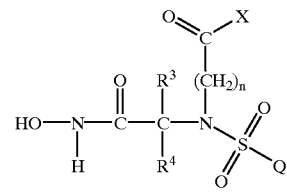

wherein n, X, $R^3$, $R^4$ and Q are as defined above, useful in the treatment of a condition selected from the group consisting of arthritis, cancer, tissue ulceration, macular degeneration, restenosis, periodontal disease, epidermolysis bullosa, scleritis, and other diseases characterized by matrix metalloproteinase activity, AIDS, sepsis, septic shock and other diseases involving the production of TNF. In addition, the compounds of the present invention may be used in combination therapy with standard non-steroidal anti-inflammatory drugs (NSAID'S) and analgesics, and in combination with cytotoxic drugs such as adriamycin, daunomycin, cis-platinum, etoposide, taxol, taxotere and other alkaloids, such as vincristine, in the treatment of cancer.

10 Claims, No Drawings

ARYLSULFONYLAMINO HYDROXAMIC ACID DERIVATIVES

The present application is a 371 application of International Patent Application PCT/IB97/00924 filed Jul. 25, 1997 (which published as WO 98/07697), which was a continuation of U.S. provisional application Ser. No. 60/024,675, filed Aug. 23, 1996.

BACKGROUND OF THE INVENTION

The present invention relates to arylsulfonylamino hydroxamic acid derivatives which are inhibitors of matrix metalloproteinases or the production of tumor necrosis factor (TNF) and as such are useful in the treatment of a condition selected from the group consisting of arthritis, cancer, tissue, ulceration, restenosis, periodontal disease, epidermolysis bullosa, scleritis and other diseases characterized by matrix metalloproteinase activity, AIDS, sepsis, septic shock and other diseases involving the production of TNF. In addition, the compounds of the present invention may be used in combination therapy with standard non-steroidal anti-inflammatory drugs (hereinafter NSAID'S) and analgesics for the treatment of arthritis, and in combination with cytotoxic drugs such as adriamycin, daunomycin, cis-platinum, etoposide, taxol, taxotere and alkaloids, such as vincristine, in the treatment of cancer.

This invention also relates to a method of using such compounds in the treatment of the above diseases in mammals, especially humans, and to pharmaceutical compositions useful therefor.

There are a number of enzymes which effect the breakdown of structural proteins and which are structurally related metalloproteases. Matrix-degrading matalloproteinases, such as gelatinase, stromelysin and collagenase, are involved in tissue matrix degradation (e.g. collagen collapse) and have been implicated in many pathological conditions involving abnormal connective tissue and basement membrane matrix metabolism, such as arthritis (e.g. osteoarthritis and rheumatoid arthritis), tissue ulceration (e.g. corneal, epidermal and gastric ulceration), abnormal wound healing, periodontal disease, bone disease (e.g. Paget's disease and osteoporosis), tumor metastasis or invasion, as well as HIV-infection (*J. Leuk. Biol.*, 52 (2): 244–248, 1992).

Tumor necrosis factor is recognized to be involved in many infectious and auto-immune diseases (W. Fiers, *FEBS Letters*, 1991, 285, 199). Furthermore, it has been shown that TNF is the prime mediator of the inflammatory response seen in sepsis and septic shock (C. E. Spooner et al., *Clinical Immunology and Immunopathology*, 1992, 62 S11).

SUMMARY OF THE INVENTION

The present invention relates to a compound of the formula

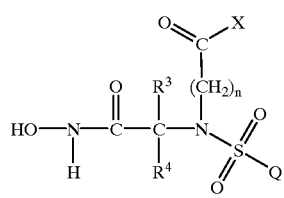

I or the pharmaceutically acceptable salts thereof, wherein n is 1 or 6;

X is $OR^1$ wherein $R^1$ is as defined below; azetidinyl, pyrrolidinyl, piperidinyl, morpholinyl, thiomorpholinyl, indolinyl, isoindolinyl, tetrahydroquinolinyl, tetrahydroisoquinolinyl, piperazinyl or a bridged diazabicycloalkyl ring selected from the group consisting of

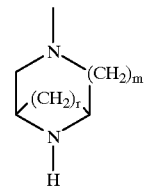

a

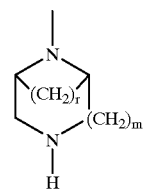

b

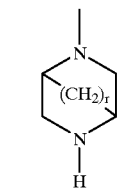

c

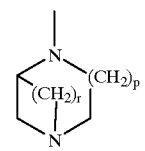

d

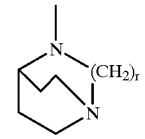

e wherein r is 1, 2 or 3;

m is 1 or 2; and p is 0 or 1;

wherein each heterocyclic group may optionally be substituted by one or two groups selected from hydroxy, $(C_1-C_6)$ alkyl, $(C_1-C_6)$alkoxy, $(C_1-C_{10})$acyl, $(C_1-C_{10})$acyloxy, $(C_6-C_{10})$aryl, $(C_5-C_9)$heteroaryl, $(C_6-C_{10})$aryl$(C_1-C_6)$ alkyl, $(C_5-C_9)$heteroaryl $(C_1-C_6)$alkyl, hydroxy $(C_1-C_6)$ alkyl, $(C_1-C_6)$alkoxy $(C_1-C_6)$alkyl, $(C_1-C_6)$acyloxy $(C_1-C_6)$alkyl, $(C_1-C_6)$alkylthio, $(C_1-C_6)$alkylthio $(C_1-C_6)$ alkyl, $(C_6-C_{10})$arylthio, $(C_6-C_{10})$ arylthio$(C_1-C_6)$alkyl, $R^9R^{10}N$, $R^9R^{10}NSO_2$, $R^9R^{10}NCO$, $R^9R^{10}NCO(C_1-C_6)$alkyl wherein $R^9$ and $R^{10}$ are each independently hydrogen, $(C_1-C_6)$alkyl, $(C_6-C_{10})$aryl, $(C_5-C_9)$heteroaryl, $(C_6-C_{10})$ aryl $(C_1-C_6)$alkyl or $(C_5-C_9)$heteroaryl $(C_1-C_6)$alkyl or $R^9$ and $R^{10}$ may be taken together with the nitrogen to which they are attached to form an azetidinyl, pyrrolidinyl, piperidinyl, morpholinyl or thiomorpolinyl ring; $R^{12}SO_2$, $R^{12}SO_2NH$ wherein $R^{12}$ is trifluoromethyl, $(C_1-C_6)$alkyl, $(C_6-C_{10})$aryl, $(C_5-C_9)$heteroaryl, $(C_6-C_{10})$aryl$(C_1-C_6)$alkyl or $(C_5-C_9)$heteroaryl $(C_1-C_6)$alkyl; $R^{13}CONR^9$ wherein $R^9$ is as defined above and $R^{13}$ is hydrogen, $(C_1-C_6)$alkyl, $(C_1-C_6)$alkoxy, $(C_6-C_{10})$ aryl, $(C_5-C_9)$heteroaryl, $(C_1-C_6)$aryl$(C_1-C_6)$alkyl$(C_6-C_{10})$aryl$(C_1-C_6)$alkoxy or $(C_5-C_9)$heteroaryl$(C_1-C_6)$alkyl; $R^{14}OOC$, $R^{14}OOC(C_1-C_6)$alkyl wherein $R^{14}$ is $(C_1-C_6)$alkyl, $(C_6-C_{10})$aryl, $(C_5-C_9)$heteroaryl, $(C_6-C_{10})$aryl $(C_1-C_6)$alkyl, 5-indanyl, $CHR^5OCOR^6$ wherein $R^5$ is hydrogen or $(C_1-C_6)$alkyl and $R^6$ is $(C_1-C_6)$alkyl, $(C_1-C_6)$alkoxy or $(C_6-C_{10})$aryl; $CH_2CONR^7R^8$ wherein $R^7$ and $R^8$ are each independently hydrogen or $(C_1-C_6)$alkyl or may be taken together with the nitrogen to which they are attached to form an azetidinyl, pyrrolidinyl, piperidinyl, morpholinyl or thiomorpholinyl ring; or $R^{15}O$ $(C_1-C_6)$alkyl wherein $R^{15}$ is $H_2N(CHR^{16})CO$ wherein $R^{16}$ is the side chain of a natural D- or L-amino acid;

$R^1$ is $(C_6-C_{10})$aryl, $(C_5-C_9)$heteroaryl, $(C_6-C_{10})$aryl $(C_1-C_6)$alkyl, 5-indanyl, $CHR^5OCOR^6$ or $CH_2CONR^7R^8$ wherein $R^5$, $R^6$, $R^7$ and $R^8$ are as defined above;

$R^3$ and $R^4$ are each independently selected from the group consisting of hydrogen, $(C_1-C_6)$alkyl, trifluoromethyl, trifluoromethyl$(C_1-C_6)$alkyl, $(C_1-C_6)$alkyl (difluoromethylene), $(C_1-C_3)$alkyl(difluoromethylene $(C_1-C_3)$alkyl, $(C_6-C_{10})$aryl, $(C_5-C_9)$heteroaryl, $(C_6-C_{10})$aryl$(C_1-C_6)$alkyl, $(C_5-C_9)$heteroaryl$(C_1-C_6)$alkyl, $(C_6-C_{10})$aryl$(C_6-C_{10})$aryl, $(C_6-C_{10})$aryl$(C_6-C_{10})$aryl$(C_1-C_6)$alkyl, $(C_3-C_6)$cycloalkyl, $(C_3-C_6)$cycloalkyl$(C_1-C_6)$alkyl, hydroxy$(C_1-C_6)$alkyl, $(C_1-C_{10})$acyloxy$(C_1-C_6)$alkyl, $(C_1-C_6)$alkoxy $(C_1-C_6)$alkyl, $(C_1-C_{10})$acylamino$(C_1-C_6)$alkyl, piperidyl, $(C_1-C_6)$alkylpiperidyl, $(C_6-C_{10})$aryl$(C_1-C_6)$alkoxy$(C_1-C_6)$alkyl, $(C_5-C_9)$heteroaryl$(C_1-C_6)$alkoxy $(C_1-C_6)$alkyl, $(C_1-C_6)$alkylthio$(C_1-C_6)$alkyl, $(C_6-C_{10})$arylthio$(C_1-C_6)$alkyl, $(C_1-C_6)$alkylsulfinyl$(C_1-C_6)$ alkyl, $(C_6-C_{10})$arylsulfinyl$(C_1-C_6)$alkyl, $(C_1-C_6)$alkylsulfonyl$(C_1-C_6)$alkyl, $(C_6-C_{10})$arylsulfonyl $(C_1-C_6)$alkyl, amino$(C_1-C_6)$alkyl, $(C_1-C_6)$alkylamino $(C_1-C_6)$alkyl, $((C_1-C_6)$alkylamino$)_2(C_1-C_6)$alkyl, $R^{17}CO(C_1-C_6)$alkyl wherein $R^{17}$ is $R^{14}O$ or $R^7R^8N$ wherein $R^7$, $R^8$ and $R^{14}$ are as defined above; or $R^{18}(C_1-C_6)$alkyl wherein $R^{18}$ is piperazinyl, $(C_1-C_{10})$acylpiperazinyl, $(C_6-C_{10})$arylpiperazinyl, $(C_5-C_9)$heteroarylpiperazinyl,$(C_1-C_6)$alkylpiperazinyl, $(C_6-C_{10})$aryl$(C_1-C_6)$alkylpiperazinyl, $(C_5-C_9)$heteroaryl$(C_1-C_6)$alkylpiperazinyl, morpholinyl, thiomorpholinyl, piperidinyl, pyrrolidinyl, piperidyl, $(C_1-C_6)$alkylpiperidyl, $(C_6-C_{10})$arylpiperidyl, $(C_5-C_9)$heteroarylpiperidyl, $(C_6-C_{10})$aryl$(C_1-C_6)$alkylpiperidyl, $(C_5-C_9)$heteroaryl$(C_1-C_6)$alkylpiperidyl or $(C_1-C_{10})$acylpiperidyl;

or $R^3$ and $R^4$ may be taken together to form a $(C_3-C_6)$cycloalkyl, oxacyclohexyl, thiocyclohexyl, indanyl or tetralinyl ring or a group of the formula

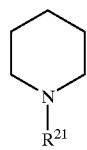

wherein $R^{21}$ is hydrogen, $(C_1-C_{10})$acyl, $(C_1-C_6)$alkyl, $(C_6-C_{10})$aryl$(C_1-C_6)$alkyl, $(C_5-C_9)$heteroaryl$(C_1-C_6)$alkyl or $(C_1-C_6)$alkylsulfonyl; and Q is $(C_1-C_6)$alkyl, $(C_6-C_{10})$aryl, $(C_6-C_{10})$aryloxy $(C_6-C_{10})$aryl, $(C_6-C_{10})$aryl$(C_6-C_{10})$aryl, $(C_6-C_{10})$aryl $(C_6-C_{10})$aryl$(C_1-C_6)$alkyl, $(C_6-C_{10})$aryloxy$(C_5-C_9)$ heteroaryl, $(C_5-C_9)$heteroaryl, $(C_1-C_6)$alkyl$(C_6-C_{10})$ aryl, $(C_1-C_6)$alkoxy$(C_6-C_{10})$aryl, $(C_6-C_{10})$aryl $(C_1-C_6)$alkoxy$(C_6-C_{10})$aryl, $(C_6-C_{10})$aryl$(C_1-C_6)$ alkoxy$(C_1-C_6)$alkyl, $(C_5-C_9)$heteroaryloxy$(C_6-C_{10})$ aryl, $(C_1-C_6)$alkyl$(C_5-C_9)$heteroaryl, $(C_1-C_6)$alkoxy $(C_5-C_9)$heteroaryl, $(C_6-C_{10})$aryl$(C_1-C_6)$alkoxy $(C_5-C_9)$heteroaryl, $(C_5-C_9)$heteroaryloxy$(C_5-C_9)$ heteroaryl, $(C_6-C_{10})$aryloxy$(C_1-C_6)$alkyl, $(C_5-C_9)$ heteroaryloxy$(C_1-C_6)$alkyl, $(C_1-C_6)$alkyl$(C_6-C_{10})$ aryloxy$(C_6-C_{10})$aryl, $(C_1-C_6)$alkyl$(C_5-C_9)$ heteroaryloxy$(C_6-C_{10})$aryl, $(C_1-C_6)$alkyl$(C_5-C_9)$ aryloxy$(C_5-C_9)$heteroaryl, $(C_1-C_6)$alkoxy$(C_6-C_{10})$ aryloxy$(C_6-C_{10})$aryl, $(C_1-C_6)$alkoxy$(C_5-C_9)$ heteroaryloxy$(C_6-C_{10})$aryl or $(C_1-C_6)$alkoxy$(C_6-C_{10})$ aryloxy$(C_5-C_9)$heteroaryl wherein each aryl group is optionally substituted by fluoro, chloro, bromo $(C_1-C_6)$ alkyl, $(C_1-C_6)$alkoxy or perfluoro$(C_1-C_3)$alkyl;

with the proviso that X must be substituted when defined as azetidinyl, pyrrolidinyl, morpholinyl, thiomorpholinyl, indolinyl, isoindolinyl, tetrahydroquinolinyl, tetrahydroisoquinolinyl, piperazinyl, $(C_1-C_{10})$acylpiperazinyl, $(C_1-C_6)$ alkylpiperazinyl, $(C_6-C_{10})$arylpiperazinyl, $(C_5-C_9)$ heteroarylpiperazinyl or a bridged diazabicycloalkyl ring.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl, optionally substituted by 1 to 3 substituents selected from the group consisting of fluoro, chloro, trifluoromethyl, $(C_1-C_6)$alkoxy, $(C_6-C_{10})$aryloxy, trifluoromethoxy, difluoromethoxy and $(C_1-C_6)$alkyl.

The term "heteroaryl", as used herein, unless otherwise indicated, includes an organic radical derived from an aromatic heterocyclic compound by removal of one hydrogen, such as pyridyl, furyl, pyroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, optionally substituted by 1 to 2 substituents selected from the group consisting of fluoro, chloro, trifluoromethyl, $(C_1-C_6)$alkoxy, $(C_6-C_{10})$aryloxy, trifluoromethoxy, difluoromethoxy and $(C_1-C_6)$alkyl.

The term "acyl", as used herein, unless otherwise indicated, includes a radical of the general formula RCO wherein R is alkyl, alkoxy, aryl, arylalkyl or arylalkyloxy and the terms "alkyl" or "aryl" are as defined above.

The term "acyloxy", as used herein, includes O-acyl groups wherein "acyl" is defined above.

The term "D- or L-amino acid", as used herein, unless otherwise indicated, includes glycine, alanine, valine, leucine, isoleucine, phenylalanine, asparagine, glutamine, tryptophan, proline, serine, threonine, tyrosine, hydroxyproline, cysteine, cystine, methionine, aspartic acid, glutamic acid, lysine, arginine or histidine.

The compound of formula I may have chiral centers and therefore exist in different enantiomeric forms. This invention relates to all optical isomers and stereoisomers of the compounds of formula I and mixtures thereof.

Preferred compounds of formula I include those wherein n is 2.

Other preferred compounds of formula I include those wherein either $R^3$ or $R^4$ is not hydrogen.

Other preferred compounds of formula I include those wherein Ar is $(C_1–C_6)$alkoxy$(C_6–C_{10})$aryl, $(C_6–C_{10})$aryl $(C_1–C_6)$alkoxy$(C_6–C_{10})$aryl, 4-fluorophenoxy$(C_6–C_{10})$aryl, 4-fluorobenzyloxy$(C_6–C_{10})$aryl or $(C_1–C_6)$alkyl$(C_6–C_{10})$ aryloxy$(C_6–C_{10})$aryl.

Other preferred compounds of formula I include those wherein X is indolinyl or piperidinyl.

More preferred compounds of formula I include those wherein n is 2; either $R^3$ or $R^4$ is not hydrogen; Ar is $(C_1–C_6)$alkoxy$(C_6–C_{10})$aryl, $(C_6–C_{10})$aryl$(C_1–C_6)$alkoxy $(C_6–C_{10})$aryl, 4-fluorophenoxy$(C_6–C_{10})$aryl, 4-fluorobenzyloxy$(C_6–C_{10})$aryl or $(C_1–C_6)$alkyl$(C_6–C_{10})$ aryloxy$(C_6–C_{10})$aryl; and X is indolinyl or piperidinyl.

Specific preferred compounds of formula I include the following:

3-[(Cyclohexylhydroxycarbamoylmethyl)-(4-methoxybenzenesulfonyl)-amino]-propionic acid indan-5-yl ester;

Acetic acid 1-{3-[(1-hydroxycarbamoyl-2-methylpropyl)-(4-methoxy-benzenesulfonyl)-amino] propionyl}piperidin-4-yl ester;

2-Cyclohexyl-N-hydroxy-2-[[3-(4-hydroxypiperidin-1-yl)-3-oxo-propyl]-(4-methoxy-benzenesulfonyl)amino] acetamide;

Benzoic acid 1-{3-[(1-hydroxycarbamoyl-2-methylpropyl)-(4-methoxy-benzenesulfonyl)amino] propionyl}piperidin-4-yl ester;

N-Hydroxy-2-[[3-(4-hydroxypiperidin-1-yl)-3-oxopropyl]-(4-methoxybenzenesulfonyl)amino]-3-methylbutyramide;

1-{3-[(Cyclohexylhydroxycarbamoylmethyl)-(4-methoxybenzenesulfonyl)-amino]propionyl}piperidine-4-carboxylic acid;

1-{3-[(Cyclohexylhydroxycarbamoylmethyl)-(4-methoxybenzenesulfonyl)-amino]propionyl}piperidine-4-carboxylic acid ethyl ester;

2-Cyclohexyl-N-hydroxy-2-{(4-methoxybenzenesulfonyl)-[3-(4-methylaminopiperidin-1-yl)-3-oxopropyl]amino}acetamide;

3-(4-Chlorophenyl)-N-hydroxy-2-{(4-methoxybenzenesulfonyl)-[3-(4-methylaminopiperidin-1-yl)-3-oxopropyl]amino}propionamide;

3-Cyclohexyl-N-hydroxy-2-{(4-methoxybenzenesulfonyl)-[3-(4-methylaminopiperidin-1-yl)-3-oxopropyl]amino}propionamide;

N-Hydroxy-2-[{3-[4-(2-hydroxy-2-methylpropyl) piperazin-1-yl]-3-oxopropyl}-(4-methoxy-benzenesulfonyl) amino]-3-methylbutyramide;

2,2-Dimethylpropionic acid 2-(4-{3-[(1-hydroxycarbamoyl-2-methylpropyl)-(4-methoxy-benzenesulfonyl)amino]propionyl}piperazin-1-yl)ethyl ester; and Benzoic acid 2-(4-{3-[(1-hydroxycarbamoyl-2-methylpropyl)-(4-methoxybenzenesulfonyl)-amino] propionyl}piperazin-1-yl)-ethyl ester.

Other specific compounds of formula I include the following:

2-Cyclohexyl-N-hydroxy-2-[{3-[4-(2-hydroxyethyl) piperazin-1-yl]-3-oxopropyl}-(4-methoxybenzenesulfonyl) amino]acetamide;

N-Hydroxy-2-[{3-[5-(2-hydroxyethyl)-2,5-diazabicyclo [2.2.1]-hept-2-yl]-3-oxopropyl}-(4-methoxybenzenesulfonyl)amino]-3-methylbutyramide;

2-{(4-Benzyloxybenzenesulfonyl)-[3-(4-hydroxypiperidin-1-yl)-3-oxopropyl]amino}-N-hydroxy-3-methylbutyramide;

2-Cyclohexyl-2-{[4-(4-fluorophenoxy)benzenesulfonyl]-[3-(4-hydroxypiperidin-1-yl)-3-oxopropyl]-amino}-N-hydroxyacetamide;

2-{[4-(4-Butylphenoxy)benzenesulfonyl]-[3-(4-hydroxypiperidin-1-yl)-3-oxopropyl]-amino}-N-hydroxy-3-methylbutyramide;

1-{(4-methoxybenzenesulfonyl)-[3-(4-methylaminopiperidin-1-yl)-3-oxopropyl]amino}-cyclopentanecarboxylic acid hydroxyamide;

4-{3-[(1-Hydroxycarbamoyl-2-methylpropyl)-(4-methoxybenzenesulfonyl)amino]-propionyl}piperazine-2-carboxylic acid ethyl ester;

3-[(Cyclohexylhydroxycarbamoylmethyl)-(4-methoxybenzenesulfonyl)amino]propionic acid ethoxycarbonyloxymethyl ester;

3-[(1-Hydroxycarbamoylpentyl)-(4-methoxybenzenesulfonyl)amino]propionic acid ethoxycarbonyloxymethyl ester;

3-[[4-(4-Fluorobenzyloxy)-benzenesulfonyl]-(1-hydroxycarbamoyl-2-methyl-propyl)-amino]-propionic acid ethoxycarbonyloxymethyl ester; and 3-[[4-(4-Fluorophenoxy)-benzenesulfonyl]-(1-hydroxycarbamoyl-2-methyl-propyl)-amino]-propionic acid ethoxycarbonyloxymethyl ester.

The present invention also relates to a pharmaceutical composition for (a) the treatment of a condition selected from the group consisting of arthritis, cancer, synergy with cytotoxic anticancer agents, tissue ulceration, macular degeneration, restenosis, periodontal disease, epidermolysis bullosa, scleritis, in combination with standard NSAID'S and analgesics and other diseases characterized by matrix metalloproteinase activity, AIDS, sepsis, septic shock and other diseases involving the production of tumor necrosis factor (TNF) or (b) the inhibition of matrix metalloproteinases or the production of tumor necrosis factor (TNF) in a mammal, including a human, comprising an amount of a compound of formula I or a pharmaceutically acceptable salt thereof effective in such treatments and a pharmaceutically acceptable carrier.

The present invention also relates to a method for the inhibition of (a) matrix metalloproteinases or (b) the production of tumor necrosis factor (TNF) in a mammal, including a human, comprising administering to said mammal an effective amount of a compound of formula I or a pharmaceutically acceptable salt thereof.

The present invention also relates to a method for treating a condition selected from the group consisting of arthritis, cancer, tissue ulceration, macular degeneration, restenosis, periodontal disease, epidermolysis bullosa, scleritis, compounds of formula I may be used in combination with standard NSAID'S and analgesics and in combination with cytotoxic anticancer agents, and other diseases characterized by matrix metalloproteinase activity, AIDS, sepsis, septic shock and other diseases involving the production of tumor necrosis factor (TNF) in a mammal, including a human, comprising administering to said mammal an amount of a compound of formula I or a pharmaceutically acceptable salt thereof effective in treating such a condition.

DETAILED DESCRIPTION OF THE INVENTION

The following reaction Schemes illustrate the preparation of the compounds of the present invention. Unless otherwise indicated n, $R^3$, $R^4$, X and Ar in the reaction Schemes and the discussion that follow are defined as above.

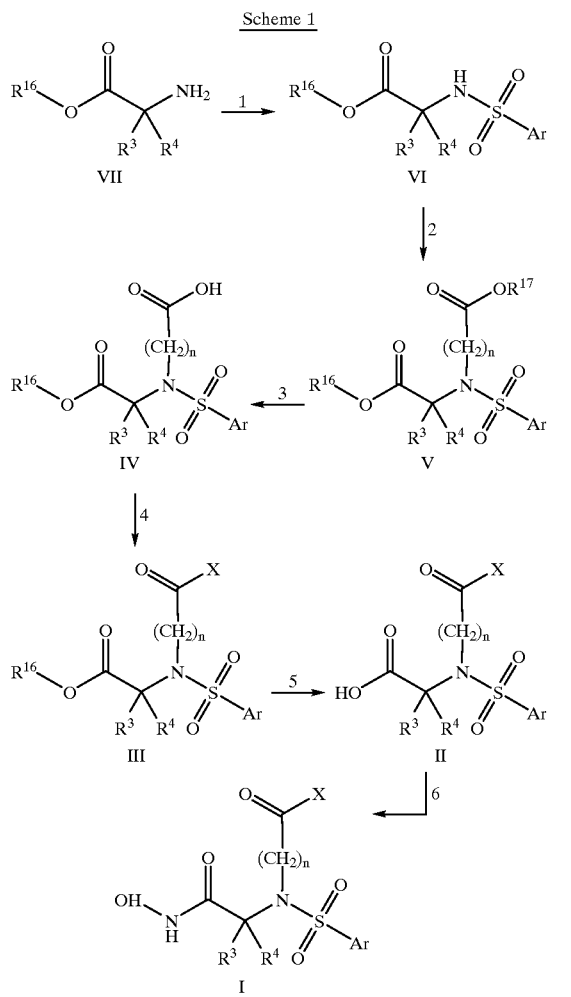

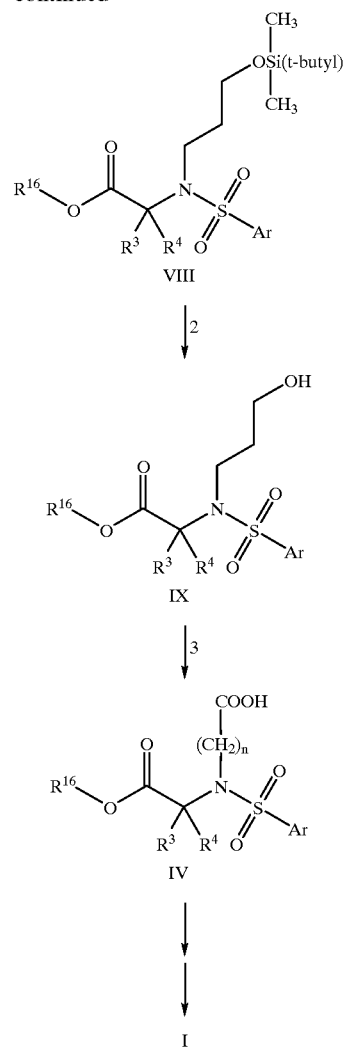

In reaction 1 of Scheme 1, the amino acid compound of formula VII, wherein $R^{16}$ is ($C_1$–$C_6$)alkyl, benzyl, allyl or tert-butyl, is converted to the corresponding compound of formula VI by reacting VII with a reactive functional derivative of an arylsulfonic acid compound, such as an arylsulfonyl chloride, in the presence of a base, such as triethylamine, and a polar solvent, such as tetrahydrofuran, dioxane, water or acetonitrile, preferably a mixture of dioxane and water. The reaction mixture is stirred, at room temperature, for a time period between about 10 minutes to about 24 hours, preferably about 60 minutes.

In reaction 2 of Scheme 1, the arylsulfonyl amino compound of formula VI, wherein $R^{16}$ is ($C_1$–$C_6$)alkyl, benzyl, allyl or tert-butyl, is converted to the corresponding compound of formula V, wherein n is 1, 3, 4, 5 or 6, by reacting VI with a reactive derivative of an alcohol of the formula

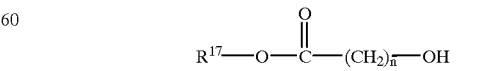

such as the chloride, bromide or iodide derivative, preferably the iodide derivative, wherein the $R^{17}$ protecting group is ($C_1$–$C_6$)alkyl, benzyl, allyl or tert-butyl, in the presence of a base such as potassium carbonate or sodium hydride, preferably sodium hydride, and a polar solvent, such as dimethylformamide. The reaction mixture is stirred, at room temperature, for a time period between about 60 minutes to about 48 hours, preferably about 18 hours. The $R^{17}$ protecting group is chosen such that it may be selectively removed in the presence of and without loss of the $R^{16}$ protecting group, therefore, $R^{17}$ cannot be the same as $R^{16}$. Removal of the $R^{17}$ protecting group from the compound of formula V to give the corresponding carboxylic acid of formula IV, in reaction 3 of Scheme 1, is carried out under conditions appropriate for that particular $R^{17}$ protecting group in use which will not affect the $R^{16}$ protecting group. Such conditions include; (a) saponification where $R^{17}$ is $(C_1-C_6)$alkyl and $R^{16}$ is tert-butyl, (b) hydrogenolysis where $R^{17}$ is benzyl and $R^{16}$ is tert-butyl or $(C_1-C_6)$alkyl, (c) treatment with a strong acid, such as trifluoroacetic acid or hydrochloric acid where $R^{17}$ is tert-butyl and $R^{16}$ is $(C_1-C_6)$alkyl, benzyl or allyl, or (d) treatment with tributyltinhydride and acetic acid in the presence of catalytic bis(triphenylphosphine) palladium (II) chloride where $R^{17}$ is allyl and $R^{16}$ is $(C_1-C_6)$ alkyl, benzyl or tert-butyl.

In reaction 4 of Scheme 1, the carboxylic acid of formula IV is condensed with a compound of the formula HX or the salt thereof, wherein X is as defined above, to give the corresponding amide compound of formula III. The formation of amides from primary or secondary amines or ammonia and carboxylic acids is achieved by conversion of the carboxylic acid to an activated functional derivative which subsequently undergoes reaction with a primary or secondary amine or ammonia to form the amide. The activated functional derivative may be isolated prior to reaction with the primary or secondary amine or ammonia. Alternatively, the carboxylic acid may be treated with oxalyl chloride or thionyl chloride, neat or in an inert solvent, such as chloroform, at a temperature between about 25° C. to about 80° C., preferably about 50° C., to give the corresponding acid chloride functional derivative. The inert solvent and any remaining oxalyl chloride or thionyl chloride is then removed by evaporation under vacuum. The remaining acid chloride functional derivative is then reacted with the primary or secondary amine or ammonia in an inert solvent, such as methylene chloride, to form the amide. The preferred method for the condensation of the carboxylic acid of formula IV with a compound of the formula HX, wherein X is as defined above, to provide the corresponding compound of formula III is the treatment of IV with (benzotriazol-1-yloxy)tris(dimethylamino) phosphonium hexafluorophosphate in the presence of a base, such as triethylamine, to provide the benzotriazol-1-oxy ester in situ which, in turn, reacts with the compound of the formula HX, in an inert solvent, such as methylene chloride, at room temperature to give the compound of formula III.

Removal of the $R^{16}$ protecting group from the compound of formula III to give the corresponding carboxylic acid of formula II, in reaction 5 of Scheme 1, is carried out under conditions appropriate for the particular $R^{16}$ protecting group in use. Such conditions include; (a) saponification where $R^{16}$ is lower alkyl, (b) hydrogenolysis where $R^{16}$ is benzyl, (c) treatment with a strong acid, such as trifluoroacetic acid or hydrochloric acid, where $R^{16}$ is tert-butyl, or (d) treatment with tributyltinhydride and acetic acid in the presence of catalyst bis(triphenylphosphine) palladium (II) chloride where $R^{16}$ is allyl.

In reaction 6 of Scheme 1, the carboxylic acid compound of formula II is converted to the hydroxamic acid compound of formula I by treating II with 1-(3-dimethylaminopropyl)-3-ethylcarbodiimide and 1-hydroxybenztriazole in a polar solvent, such as dimethylformamide, followed by the addition of hydroxylamine to the reaction mixture after a time period between about 15 minutes to about 1 hour, preferably about 30 minutes. The hydroxylamine is preferably generated in situ from a salt from, such as hydroxylamine hydrochloride, in the presence of a base, such as N-methylmorpholine. Alternatively, a protected derivative of hydroxylamine or its salt form, where the hydroxyl group is protected as a tert-butyl, benzyl, allyl or trimethylsilylether, may be used in the presence of (benzotriazol-1-yloxy)tris-(dimethylamino) phosphonium hexafluorophosphate and a base, such as N-methylmorpholine. Removal of the hydroxylamine protecting group is carried out by hydrogenolysis for a benzyl protecting group or treatment with a strong acid, such as trifluoroacetic acid, for a tert-butyl protecting group. The allyl protecting group may be removed by treatment with tributyltinhydride and acetic acid in the presence of catalytic bis(triphenylphosphine) palladium (II) chloride. The 2-trimethylsilylethyl ether may be removed by reaction with a strong acid, such as trifluoroacetic acid or by reaction with a fluoride source such as boron trifluoride etherate. N,O-bis (4-methoxybenzyl)hydroxylamine may also be used as the protected hydroxylamine derivative where deprotection is achieved using a mixture of methanesulfonic acid and trifluoroacetic acid.

In reaction 1 of Scheme 2, the arylsulfonylamino compound of formula VI, wherein $R^{16}$ is $(C_1-C_6)$alkyl, benzyl or tert-butyl, is converted to the corresponding compound of formula VIII by reacting VI with a reactive functional derivative, such as the halide, preferably the iodide derivative, of 3-(tert-butyldimethylsilyloxy)-1-propanol in the presence of a base, such as sodium hydride. The reaction is stirred in a polar solvent, such as dimethylformamide, at room temperature, for a time period between about 2 hours to about 48 hours, preferably about 18 hours.

In reaction 2 of Scheme 2, the compound of formula VIII is converted to the alcohol compound of formula IX by treatment of VIII with an excess of an acid, such as acetic acid, or an excess of a Lewis acid, such as boron trifluoride etherate. When using an acid, such as acetic acid, water is added and a water-soluble cosolvent, such as tetrahydrofuran, can be added to promote solubility. The reaction is stirred for a time period between about 18 hours to about 72 hours, preferably about 24 hours, at a temperature between about room temperature to about 60° C., preferably about 50° C. When using a Lewis acid, such as boron trifluoride etherate, the reaction is stirred in a solvent, such as methylene chloride, for a time period between about 10 minutes to about 6 hours, preferably about 20 minutes, at a temperature between about −20° C. to about room temperature, preferably about room temperature.

In reaction 3 of Scheme 2, the alcohol compound of formula IX is oxidized to the carboxylic acid compound of formula IV, wherein n is 2, by reacting IX with an excess of sodium periodate and a catalytic amount of ruthenium trichloride in a solvent mixture consisting of acetonitrile, water and carbon tetrachloride, at room temperature, for a time period between about 1 hour to about 24 hours, preferably about 4 hours.

The compound of formula IV, wherein n is 2, is further reacted to provide the hydroxamic acid compound of formula I, wherein n is 2, according to the procedure described above in reactions 4, 5 and 6 of Scheme 1.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methylammonium slats.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure.

The ability of the compounds of formula I or their pharmaceutically acceptable salts (hereinafter also referred to as the compounds of the present invention) to inhibit matrix metalloproteinases or the production of tumor nucrosis factor (TNF) and, consequently, demonstrate their effectiveness for treating diseases characterized by matrix metalloproteinase or the production of tumor necrosis factor is shown by the following in vitro assay tests.

Biological Assay

Inhibition of Human Collagenase (MMP-1)

Human recombinant collagenase is activated with trypsin using the following ratio: 10 μg trypsin per 100 μg of collagenase. The trypsin and collagenase are incubated at room temperature for 10 minutes then a five fold excess (50 μg/10 μg trypsin) of soybean trypsin inhibitor is added.

10 mM stock solutions of inhibitors are made up in dimethyl sulfoxide and then diluted using the following Scheme:

10 mM→120 μM→12 μM→1.2 μM→0.12 μM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) ware set up in wells D1–D6 and blanks (no enzyme, no inhibitors) are set in wells D7–D12.

Collagenase is diluted to 400 ng/ml and 25 μl is then added to appropriate wells of the microfluor plate. Final concentration of collagenase in the assay is 100 ng/ml.

Substrate (DNP-Pro-Cha-Gly-Cys(Me)-His-Ala-Lys (NMA)-NH$_2$) is made as a 5 mM stock in dimethyl sulfoxide and then diluted to 20 μM in assay buffer. The assay is initiated by the addition of 50 μl substrate per well of the microfluor plate to give a final concentration of 10 μM.

Fluorescence readings (360 nM excitation, 460 nm emission) were taken at time 0 and then at 20 minute intervals. The assay is conducted at room temperature with a typical assay time of 3 hours.

Fluorescence vs time is then plotted for both the blank and collagenase containing samples (data from triplicate determinations is averaged). A time point that provides a good signal (the blank) and that is on a linear part of the curve (usually around 120 minutes) is chosen to determine IC$_{50}$ values. The zero time is used as a blank for each compound at each concentration and these values are subtracted from the 120 minute data. Data is plotted as inhibitor concentration vs % control (inhibitor fluorescence divided by fluorescence of collagenase alone×100). IC$_{50}$'s are determined from the concentration of inhibitor that gives a signal that is 50% of the control.

If IC$_{50}$'s are reported to be <0.03 μM then the inhibitors are assayed at concentrations of 0.3 μM, 0.03 μM, 0.03 μM and 0.003 μM.

Inhibition of Gelatinase (MMP-2)

Inhibition of gelatinase activity is assayed using the Dnp-Pro-Cha-Gly-Cys(Me)-His-Ala-Lys(NMA)-NH$_2$ substrate (10 μM) under the same conditions as inhibition of human collagenase (MMP-1).

72 kD gelatinase is activated with 1 mM APMA (p-aminophenyl mercuric acetate) for 15 hours at 4° C. and is diluted to give a final concentration in the assay of 100 mg/ml. Inhibitors are diluted as for inhibition of human collagenase (MMP-1) to give final concentrations in the assay of 30 μM, 3 μM, 0.3 μM and 0.03 μM. Each concentration is done in triplicate.

Fluorescence readings (360 nm excitation, 460 emission) are taken at time zero and then at 20 minutes intervals for 4 hours.

IC$_{50}$'s are determined as per inhibition of human collagenase (MMP-1). If IC$_{50}$'s are reported to be less than 0.03 μM, then the inhibitors are assayed at final concentrations of 0.3 μM, 0.03 μM, 0.003 μM and 0.003 μM.

Inhibition of Stromelysin Activity (MMP-3)

Inhibition of stromelysin activity is based on a modified spectrophotometric assay described by Weingarten and Feder (Weingarten, H. and Feder, J., Spectrophotometric Assay for Vertebrate Collagenase, Anal. Biochem. 147, 437–440 (1985)). Hydrolysis of the thio peptolide substrate [Ac-Pro-Leu-Gly-SCH[CH$_2$CH(CH$_3$)$_2$]CO-Leu-Gly-OC$_2$H$_5$] yields a mercaptan fragment that can be monitored in the presence of Ellman's reagent.

Human recombinant prostromelysin is activated with trypsin using a ratio of 1 μl of a 10 mg/ml trypsin stock per 26 μg of stromelysin. The trypsin and stromelysin are incubated at 37° C. for 15 minutes followed by 10 μl of 10 mg/ml soybean trypsin inhibitor for 10 minutes at 37° C. for 10 minutes at 37° C. to quench trypsin activity.

Assays are conducted in a total volume of 250 μl of assay buffer (200 mM sodium chloride, 50 mM MES, and 10 mM calcium chloride, pH 6.0) in 96-well microliter plates. Activated stromelysin is diluted in assay buffer to 25 μg/ml. Ellman's reagent (3-Carboxy-4-nitrophenyl disulfide) is made as a 1M stock in dimethyl formamide and diluted to 5 mM in assay buffer with 50 μl per well yielding at 1 mM final concentration.

10 mM stock solutions of inhibitors are made in dimethyl sulfoxide and diluted serially in assay buffer such that addition of 50 μL to the appropriate wells yields final concentrations of 3 μM, 0.3 μM, 0.003 μM and 0.0003 μM. All conditions are completed in triplicate.

A 300 mM dimethyl sulfoxide stock solution of the peptide substrate is diluted to 15 mM in assay buffer and the assay is initiated by addition of 50 μl to each well to give a final concentration of 3 mM substrate. Blanks consist of the peptide substrate and Ellman's reagent without the enzyme. Product formation was monitored at 405 nm with a Molecular Devices UVmax plate reader.

IC$_{50}$ values were determined in the same manner as for collagenase.

Inhibition of MMP-13

Human recombinant MMP-13 is activated with 2 mM APMA (p-aminophenyl mercuric acetate) for 1.5 hours, at 37° C. and is diluted to 400 mg/ml in assay buffer (50 mM Tris, pH 7.5, 200 mM sodium chloride, 5 mM calcium chloride, 20 μM zinc chloride, 0.02% brij). Twenty-five microliters of diluted enzymes is added per well of a 96 well microfluor plate. The enzyme is then diluted in a 1:4 ratio in the assay by the addition of inhibitor and substrate to give a final concentration in the assay of 100 mg/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 $\mu$M, 3 $\mu$M, 0.3 $\mu$M, and 0.03 $\mu$M.

Substrate (Dnp-Pro-Cha-Gly-Cys(Me)-His-Ala-Lys (NMA)-NH$_2$) is prepared as for inhibition of human collagenase (MMP-1) and 50 $\mu$l is added to each well to give a final assay concentration of 10 $\mu$M. Fluorescence readings (360 nM excitation; 450 emission) are taken at time 0 and every 5 minutes for 1 hour.

Positive controls consist of enzyme and substrate with no inhibitor and blanks consist of substrate only.

IC$_{50}$'s are determined as per inhibition of human collagenase (MMP-1). If IC$_{50}$'s are reported to be less than 0.03 $\mu$M, inhibitors are then assayed at final concentrations of 0.3 $\mu$M, 0.03 $\mu$M, 0.003 $\mu$M and 0.0003 $\mu$M.

Inhibition of TNF Production

The ability of the compounds or the pharmaceutically acceptable salts thereof to inhibit the production of TNF and, consequently, demonstrate their effectiveness for treating diseases involving the production of TNF is shown by the following in vitro assay:

Human mononuclear cells were isolated from anti-coagulated human blood using a one-step Ficoll-hypaque separation technique. (2) The mononuclear cells were washed three times in Hanks balanced salt solution (HBSS) with divalent cations and resuspended to a density of 2×10$^6$/ml in HBSS containing 1% BSA. Differential counts determined using the Abbott Cell Dyn 3500 analyzer indicated that monocytes ranged from 17 to 24% of the total cells in these preparations.

180$\mu$ of the cell suspension was aliquoted into flate bottom 96 well plates (Costar). Additions of compounds and LPS (100 ng/ml final concentration) gave a final volume of 200 $\mu$l. All conditions were performed in triplicate. After a four hour incubation at 37° C. in an humidified CO$_2$ incubator, plates were removed and centrifuged (10 minutes at approximately 250×g) and the supernatants removed and assayed for TNF$\alpha$ using the R&D ELISA Kit.

For administration to mammals, including humans, for the inhibition of matrix metalloproteinases or the production of tumor nucrosis factor (TNF), a variety of conventional routes may be used including orally, parenterally and topically. In general, the active compound will be administered orally or parenterally at dosages between about 0.1 and 25 mg/kg body weight of the subject to be treated per day, preferably from about 0.3 to 5 mg/kg. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. In the case of animals, they are advantageously contained in an animal feed or drinking water in a concentration of 5–5000 ppm, preferably 25 to 500 ppm.

For parenteral administration (intramuscular, intrapertioneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. In the case of animals, compounds can be administered intramuscularly or subcutaneously at dosage levels of about 0.1 to 50 mg/kg/day, advantageously 0.2 to 10 mg/kg/day given in a single dose or up to 3 divided doses.

The present invention is illustrated by the following examples, but it is not limited to the details thereof.

EXAMPLE 1

2-Cyclohexyl-N-hydroxy-2-{(4-methoxybenzenesulfonyl)-[3-(4-methyl-aminopiperidin-1-yl)-3-oxopropyl]amino}acetamide (A) To a solution of D-cyclohexylglycine benzyl ester hydrochloride (17.0 grams, 59.9 mmol) and triethylamine (17.6 mL, 126.3 mmol) in water (60 mL) and 1,4-dioxane (100 mL) was added 4-methoxybenzenesulfonyl chloride (13.0 grams, 62.9 mmol). The mixture was stirred at room temperature for 16 hours and then most of the solvent was removed by evaporation under vacuum. The mixture was diluted with ethyl acetate and was washed successively with dilute hydrochloric acid solution, water, saturated sodium bicarbonate solution, and brine. The organic solution was dried over magnesium sulfate and concentrated to leave N-(4-methoxybenzenesulfonyl)-D-cyclohexylglycine benzyl ester as a white solid, 24.51 grams (99%).

(B) N-(4-Methoxybenzenesulfonyl)-D-cyclohexylglycine benzyl ester (12.0 grams, 29.16 mmol) was added to a suspension of sodium hydride (0.78 grams, 32.5 mmol) in dry N,N-dimethylformamide (100 ml) and, after 20 minutes, tert-butyl-(3-iodopropoxy)-dimethylsilane(9.2 grams, 30.6 mmol) was added. The resulting mixture was stirred at room temperature for 16 hours and was then quenched by addition of saturated ammonium chloride solution. The N,N-dimethylformamide was then removed by evaporation under vacuum. The residue was taken up in diethyl ether and washed successively with dilute hydrochloric acid solution, water and brine. After drying over magnesium sulfate, the diethyl ether was evaporated under vacuum to afford a yellow oil from which [[3-(tert-butyldimethylsilanyloxy) propyl](4-methoxy-benzenesulfonyl)-amino] cyclohexylacetic acid benzyl ester, a clear oil (13.67 grams, 79%), was isolated by flash chromatography on silica gel eluting with 10% ethyl acetate in hexane.

(C) To a solution of [[3-(tert-butyldimethylsilanyloxy) propyl](4-methoxybenzenesulfonyl) amino] cyclohexylacetic acid benzyl ester (13.67 grams, 23.2 mmol) in methylene chloride (60 mL) at room temperature was added boron trifluoride etherate (21 mL, 171 mmol). After 20 minutes, the reaction was quenched by addition of saturated ammonium chloride solution and subsequent addition of ethyl acetate and water. The organic phase was separated, washed with brine and dried over magnesium sulfate. Evaporation of the solvent under vacuum gave an oil from which cyclohexyl[(3-hydroxypropyl)(4-methoxybenzenesulfonyl)amino]acetic acid benzyl ester, a clear oil (11.25 grams, 100%), was isolated by flash chromatography on silica gel eluting with 20% ethyl acetate in hexane and then 40% ethyl acetate in hexane.

(D) Cyclohexyl[(3-hydroxypropyl)(4-methoxybenzenesulfonyl)amino]acetic acid benzyl ester (45.8 grams, 96 mmol) and sodium periodate (92.6 grams, 433 mmol) were dissolved in a mixture of acetonitrile (345 mL), carbon tetrachloride (345 mL) and water 460 mL). While cooling in an ice bath, ruthenium trichloride monohydrate (4.4 grams, 21 mmol) was then added. The resulting mixture was mechanically stirred with ice bath cooling for 30 minutes. The bath was removed and stirring was continued at room temperature for 4 hours. The reaction mixture was diluted with ethyl acetate and filtered through diatomaceous earth. The organic layer was separated and the aqueous layer was extracted with ethyl acetate. The combined organic layers were washed with water and saturated brine. After drying over magnesium sulfate, the solvents were evaporated to give a dark oil from which 3-[(benzyloxycarbonylcyclohexylmethyl)-(4-methoxybenzenesulfonyl) amino]propionic acid, a white foam (28.1 grams, 60%), was isolated by flash chromatography on silica gel eluting sequentially with chloroform and 1% methanol in chloroform.

(E) To a solution of 3-[(benzyloxycarbonylcyclohexylmethyl)(4-methoxybenzenesulfonyl)-amino]propionic acid (1.57 grams, 3.21 mmol) in methylene chloride (45 mL) were added sequentially triethylamine (1.12 mL, 8.04 mmol), methylpiperidin-4-ylcarbamic acid tert-butyl ester (0.89 grams, 4.15 mmol) and (benzotriazol-1-yloxy)tris(dimethylamino)-phosphonium hexafluoroborate (1.56 grams, 3.53 mmol). The result mixture was stirred for 16 hours at room temperature and then diluted with methylene chloride. The solution was washed successively with 0.5M hydrochloric acid solution, saturated sodium bicarbonate solution and brine. The solution was dried over magnesium sulfate and concentrated to yield an oil which was chromatographed on silica gel eluting with 50% ethyl acetate in hexane to afford [{(3-[4-(tert-butoxycarbonylmethylamino)piperidin-1-yl]-3-oxopropyl}-(4-methoxybenzenesulfonyl) amino] cyclohexylacetic acid benzyl ester as an oil (1.89 grams, 86%).

(F) To a solution of [{3-[4-(tert-butoxycarbonylmethylamino)piperidin-1-yl]-3-oxopropyl} (4-methoxybenzenesulfonyl) amino]cyclohexylacetic acid benzylester (1.89 grams, 2.76 mmol) in ethanol (90 mL) was added 10% palladium on activated carbon (0.32 grams). The mixture was agitated under 3 atmospheres hydrogen in a Parr shaker for 2 hours. The catalyst was removed by filtration through nylon (pore size 0.45 μm) and the solvent was evaporated leaving [{3-[4-(tert-butoxycarbonylmethylamino) piperidin-1-yl]-3-oxo-propyl}(4-methoxybenzenesulfonyl)amino]cyclohexylacetic acid as a white foam (1.65 grams, 100%).

(G) To a solution of [{(3-[4-(tert-butoxycarbonylmethylamino)piperidin-1-yl]-3-oxopropyl} (4-methoxybenzenesulfonyl) amino]cyclohexylacetic acid (1.65 grams, 2.76 mmol) in methylene chloride (30 mL) were added sequentially O-benzylhydroxylamine hydrochloride (0.47 grams, 2.94 mmol), triethylamine (1.25 mL, 9.0 mmol) and (benzotriazol-1-yloxy)tris(dimethylamino) phosphonium hexafluoroborate (1.36 grams, 3.07 mmol). The resulting mixture was stirred for 24 hours at room temperature and then concentrated in vacuo. The residue was taken up in ethyl acetate and washed successively with 0.5M hydrochloric acid solution, water, saturated sodium bicarbonate solution and brine. The solution was dried over magnesium sulfate and concentrated to yield an oil which was chromatographed on silica gel eluting with 40% hexane in ethyl acetate to afford (1-{3-[(benzyloxycarbamolycyclohexylmethyl)(4-methoxybenzenesulfonyl) amino]-propionyl}piperidin-4-yl)methylcarbamic acid tert-butyl esteras a clear oil (1.86 grams, 96%).

(H) To a solution of (1-{3-[(benzyloxycarbamoylcyclohexylmethyl)(4-methoxybenzenesulfonyl) amino]propionyl}piperidin-4-yl) methylcarbamic acid tert-butyl ester (1.86 grams, 2.65 mmol) in methanol (80 mL) was added 5% palladium on barium sulfate (0.85 grams). The mixture was agitated under 3 atmospheres hydrogen in a Parr shaker for 2.5 hours. The catalyst was removed by filtration through nylon (pore size 0.45 μm) and the solvent was evaporated leaving (1-{3-[(cyclohexylhydroxycarbamoylmethyl)(4-methoxybenzenesulfonyl)amino]propionyl}piperidin-4-yl)methylcarbamic acid tert-butyl esteras a white foam (1.53 grams, 95%).

The title compounds of examples 2–8 were prepared analogously to that described in Example 1 using D-valine benzyl ester as the starting material in step A and the indicated amine in step E.

EXAMPLE 2

Acetic acid 1-{3-[(1-hydroxycarbamoyl-2-methylpropyl) (4-methoxybenze-sulfonyl)-amino]propionyl}piperidin-4-yl ester Coupled with acetic acid piperidin-4-yl ester. MS: 500 (M+1).

EXAMPLE 3

Butyric acid 1-{3-[(1-hydroxycarbamoyl-2-methylpropyl)-(4-methoxy-benzenesulfonyl)-amino] propionyl}piperidin-4-yl ester Coupled with butyric acid piperidin-4-yl ester. MS: 528 (M+1).

EXAMPLE 4

Benzoic acid 1-{3-[(1-hydroxycarbamoyl-2-methylpropyl)(4-methoxy-benzene-sulfonyl)amino] propionyl}piperidin-4-yl ester Coupled with benzoic acid piperidin-4-yl ester. MS: 562 (M+1). Analysis Calculated for $C_{27}H_{35}N_3O_8S \cdot 1.75\ H_2O$: C, 54.67; H, 6.54; N, 7.08. Found: C, 54.52, H, 6.14; N, 7.85.

EXAMPLE 5

N-Hydroxy-2-[[3-(4-hydroxypiperidin-1-yl)-3-oxopropyl]-(4-methoxy-benzene-sulfonyl) amino]-3-methylbutyramide Coupled with 4-hydroxypiperidine. MS: 458 (M+1). Analysis calculated for $C_{20}H_{31}N_3O_7S \cdot H_2O$: C, 50.51; H, 6.99; N, 8.84. Found: C, 50.04; H, 6.84; N, 9.14.

EXAMPLE 6

(1-{3-[(1-Hydroxycarbamoyl-2-methylpropyl)(4-methoxybenzenesulfonyl)-amino]-propionyl}piperidin-4-yl)-methylcarbamic acid tert-butyl ester Coupled with methyl-piperidin-4ylcarbamic acid tert-butyl ester.

EXAMPLE 7

1-{3-[(1-Hydroxycarbamoyl-2-methylpropyl)(4-methoxybenzenesulfonyl)-amino]-propionyl}piperidine-4-carboxylic acid ethyl ester Coupled with piperidine-4-carboxylic acid ethyl ester. MS: 513 (M+1).

EXAMPLE 8

(4-{3-[(1-Hydroxycarbamoyl-2-methylpropyl)(4-methoxybenzenesulfonyl)-amino]-propionyl}piperazin-1-yl)-acetic acid ethyl ester Coupled with piperazin-1-ylacetic acid ethyl ester. HRMS calculated for $C_{23}H_{37}N_4O_8S(M+1)$: 529.2332. Found: 529.2366.

The title compounds of Examples 9–10 were prepared analogously to that described in Example 1 using D-leucine benzyl ester as the starting material in step A and the indicated amine in step E.

EXAMPLE 9

(1-{3-[(1-Hydroxycarbamoyl-3-methylbutyl)(4-methoxybenzenesulfonyl)-amino]-propionyl}piperidin-4-yl)methylcarbamic acid tert-butyl ester Coupled with m ethyl-piperidin-4-ylcarbamic acid tert-butyl ester. MS: 585 (M+1).

EXAMPLE 10

1-{3-[(1-Hydroxycarbamoyl-3-methylbutyl)-(4-methoxybenzenesulfonyl)-amino]-propionyl}piperidine-4-carboxylic acid ethyl ester Coupled with piperidine-4-carboxylic acid ethyl ester. Melting point 78–80° C. MS: 528 (M+1).

The title compounds of Examples 11–13 were prepared analogously to that described in Example 1 using D-norleucine benzyl ester as the starting material in step A and the indicated amine or alcohol in step E.

EXAMPLE 11

(1-{3-[(1-Hydroxycarbamoylpentyl)(4-methoxybenzenesulfonyl)amino]-propionyl}piperidin-4-yl)methylcarbamic acid tert-butyl ester Coupled with methyl-piperidin-4-ylcarbamic acid tert-butyl ester.

EXAMPLE 12

1-{3-[(1-Hydroxycarbamoylpentyl)(4-methyoxybenzenesulfonyl)amino]-propionyl}piperidine-4-carboxylic acid ethyl ester Coupled with piperidine-4-carboxylic acid ethyl ester. MS: 528 (M+1).

EXAMPLE 13

3-[(1-Hydroxycarbamoylpentyl)(4-methoxybenzenesulfonyl)amino]-propionic acid indan-5-yl ester Coupled with 5-indanol. MS: 505 (M+1).

The title compounds of Examples 14–15 were prepared analogously to that described in Example 1 using D-tert-butylalanine benzyl ester as the starting material in step A and the indicated amine in step E.

EXAMPLE 14

(1-{3-[(1-Hydroxycarbamoyl-3,3-dimethylbutyl)-(4-methoxybenzene-sulfonyl)-amino] propionyl}piperidin-4-yl)methylcarbamic acid tert-butyl ester Coupled with methyl-piperidin-4-ylcarbamic acid tert-butyl ester. MS: 599 (M+1).

EXAMPLE 15

1-{3-[(1-Hydroxycarbamoyl-3,3-dimethylbutyl)-(4-methoxy-benzenesulfonyl)-amino] propionyl}piperidine-4-carboxylic acid ethyl ester Coupled with piperidine-4-carboxylic acid ethyl ester. MS: 542 (M+1).

The title compounds of Examples 16–18 were prepared analogously to that described in Example 1 using D-cyclohexylglycine benzyl ester as the starting material in step A and the indicated amine or alcohol in step E.

EXAMPLE 16

2-Cyclohexyl-N-hydroxy-2-[[3-(4-hydroxypiperidin-1-yl)-3-oxopropyl]-(4-methoxy-benzenesulfonyl) amino]acetamide Coupled with 4-hydroxypiperidine. MS: 498 (M+1). Analysis calculated for $C_{23}H_{35}N_3O_7S \cdot 0.5H_2O$; C, 54.53; H, 7.16; N, 8.29. Found: C, 54.21; H, 6.98; N, 8.21.

EXAMPLE 17

1-{3-[(Cyclohexylhydroxycarbamoylmethyl)(4-methoxybenzenesulfonyl)-amino] propionyl}piperidine-4-carboxylic acid ethyl ester Coupled with piperdine-4-carboxylic acid ethyl ester. MS: 554 (M+1). Analysis calculated for $C_{26}H_{39}N_3O_1S \cdot 0.5H_2O$: C, 55.59; H, 7.16; N, 7.47. Found: C, 55.53; H, 7.18; N, 7.57.

EXAMPLE 18

3-[(Cyclohexylhydroxycarbamoylmethyl)-(4-methoxybenzenesulfonyl)-amino]-propionic acid indan-5-yl ester Coupled with 5-indanol. MS: 531 (M+1). Analysis calculated for $C_{27}H_{34}N_2O_7S \cdot H_2O$: C, 59/11; H, 6.61; N, 5.10. Found: C, 59.40; H, 6.17; N, 5.06.

The title compounds of Examples 19–20 were prepared analogously to that described in Example 1 using D-phenylalanine benzyl ester as the starting material in step A and the indicated amine in step E.

EXAMPLE 19

(1-{3-[(1-Hydroxycarbamoyl-2-phenylethyl)(4-methoxybenzenesulfonyl)-amino]-propionyl}piperidin-4-yl)methylcarbamic acid tert-butyl ester Coupled with methyl-piperidin-4-ylcarbamic acid tert-butyl ester. MS: 619 (M+1).

EXAMPLE 20

1-{3-[(1-Hydroxycarbamoyl-2-phenylethyl)-(4-methoxybenzenesulfonyl)-amino]-propionyl}piperidine-4-carboxylic acid ethyl ester Coupled with piperidine-4-carboxylic acid ethyl ester. MS: 561 (M+1).

The title compounds of Examples 21–22 were prepared analogously to that described in Example 1 using D-4-fluorophenylalanine benzyl ester as the starting material in step A and the indicated amine in step E.

EXAMPLE 21

(1-{3-[[2-(4-Fluorophenyl)-1-hydroxycarbamoylethyl]-(4-methoxy-benzene-sulfonyl)amino]propionyl}piperidine-4-yl)methylcarbamic acid tert-butyl ester Coupled with methyl-piperidin-4-ylcarbamic acid tert-butyl ester.

EXAMPLE 22

1-{3-[[2-(4Fluorophenyl)-1-hydroxycarbamoylethyl](4-methoxy-benzenesulfonyl) amino]propionyl}piperidine-4-carboxylic acid ethyl ester Coupled with piperidine-4-carboxylic acid ethyl ester. MS: 580 (M+1). Analysis calculated for $C_{27}H_{34}NF_3O_8S$: C, 55.95; H, 5.91; N, 7.25. Found: C, 55.72; H, 5.79; N, 7.08.

The title compounds of Examples 23–24 were prepared analogously to that described in Example 1 using D-4-homophenylalanine benzyl ester as the starting material in step A and the indicated amine in step E.

EXAMPLE 23

(1-{3-[(1Hydroxycarbamoyl-3-phenylpropyl)-(4-methoxybenzene-sulfonyl)-amino]propionyl}piperidin-4-yl)methylcarbamic acid tert-butyl ester Coupled with tert-butyl ester using methyl-piperidin-4-ylcarbamic acid tert-butyl ester. MS: 633 (M+1).

EXAMPLE 24

1-{3-[(1-Hydroxycarbamoyl-3-phenylpropyl)-(4-methoxybenzene-sulfonyl)amino]-propionyl}piperidine-4-carboxylic acid ethyl ester Coupled with piperidine-4-carboxylic acid ethyl ester. MS: 576 (M+1).

The title compounds of Examples 27–28 were prepared analogously to that described in Example 1 using D-O-tert-butylserine benzyl ester as the starting material in step A and the indicated amine in step E.

EXAMPLE 25

(1-{3-[(2-tert-Butoxy-1-hydroxycarbamoylethyl)(4-methoxybenzene-sulfonyl)-amino]propionyl}piperidin-4-yl)methylcarbamic acid tert-butyl ester Coupled with methyl-piperidin-4-ylcarbamic acid tert-butyl ester. MS: 615 (M+1).

EXAMPLE 26

1-{3-[(2-tert-Butoxy-1-hydroxycarbamoylethyl)(4-methoxy-benzenesulfonyl)-amino]propionyl}piperidine-4-carboxylic acid ethyl ester Coupled with piperidine-4-carboxylic acid ethyl ester. MS: 558 (M+1).

The title compounds of Examples 27–28 were prepared analogously to that described in Example 1 using D-cyclohexylalanine benzyl ester as the starting material in step A and the indicated amine in step E.

EXAMPLE 27

(1-{3-[(2-Cyclohexyl-1-hydroxycarbamoylethyl)-(4-methoxy-benzene-sulfonyl)-amino]propionyl}piperidin-4-yl)methylcarbamic acid tert-butyl ester Coupled with methyl-piperidin-4-ylcarbamic acid tert-butyl ester. MS: 625 (M+1).

EXAMPLE 28

1-{3-[(2-Cyclohexyl-1-hydroxycarbamoylethyl)(4-methoxy-benzenesulfonyl)-amino]propionyl}piperidine-4-carboxylic acid ethyl ester Coupled with piperidine-4-carboxylic acid ethyl ester. MS: 568 (M+1).

The title compounds of Examples 29–30 were prepared analogously to that described in Example 1 using D-1-naphthylalanine benzyl ester as the starting material in step A and the indicated amine in step E.

EXAMPLE 29

(1-{3-[(1-Hydroxycarbamoyl-2-naphthalen-1-ylethyl)-(4-methoxy-benzenesulfonyl)amino}propionyl]piperidine-4-yl)methylcarbamic acid tert-butyl ester Coupled with methylpiperidin-4-ylcarbamic acid tert-butyl ester.

EXAMPLE 30

1-{3-[(1-Hydroxycarbamoyl-2-naphthalen-1-ylethyl)(4-methoxybenzene-sulfonyl) amino]propionyl}piperidine-4-carboxylic acid ethyl ester Coupled with piperidine-4-carboxylic acid ethyl ester. MS: 611 (M+1).

EXAMPLE 31

2-Cyclohexyl-N-hydroxy-2-{(4-methoxybenzenesulfonyl)-[3-(4-methyl-amino-piperidin-1-yl)-3-oxopropyl]-amino}acetamide A solution of 1-{3-[(cyclohexylhydroxycarbamoylmethyl)(4-methoxybenzenesulfonyl)-amino]-propionyl}piperidin-4-yl)methylcarbamic acid tert-butyl ester (1.53 grams, 2.50 mmol) in methylene chloride (70 mL) was bubbled with hydrochloric acid gas for 2 minutes. The ice bath was removed and the reaction mixture was allowed to stir at room temperature for 1 hour. The solvent was evaporated and twice methanol was added to the residue and evaporated leaving 2-cyclohexyl-N-hydroxy-{(4-methoxybenzenesulfonyl)-[3-(4-methylaminopiperidin-1-yl)-3-oxopropyl]-amino}acetamide hydrochloride dihydrate as a white solid (1.22 grams, 90%). MS: 511 (M+1). Analysis calculated for $C_{24}N_{39}ClN_4O_6S \cdot 2H_2O$: C, 49.43; H, 7.43; N, 9.61. Found: C, 49.86; H, 7.23; N, 9.69.

The title compounds of Examples 32–41 were prepared analogously to that described in Example 33 using the starting material indicated.

EXAMPLE 32

N-Hydroxy-2-{(4-methoxybenzenesulfonyl)[3-(4-methylaminopiperidin-1-yl)-3-oxopropyl]amino}-3-methylbutyramide hydrochloride Starting material: (1-{3-[(1-hydroxycarbamoyl-2-methylpropyl)(4-methoxybenzene-sulfonyl)-amino]propionyl}piperidin-4-yl)-methylcarbamic acid tert-butyl ester using methyl-piperidin-4-ylcarbamic acid tert-butyl. MS: 471 (M+1).

EXAMPLE 33

2-{(4-Methoxybenzenesulfonyl)-[3-(4-methylaminopiperidin-1-yl)-3-oxo-propyl]-amino}4-methylpentanoic acid hydroxyamide hydrochloride Starting material: (1-{3-[(1-hydroxycarbamoyl-3-methylbutyl)(4-methoxybenzenesulfonyl) amino]propionyl}piperidin-4-yl)methylcarbamic acid tert-butyl ester. Melting point 170–173° C. MS: 485 (M+1).

EXAMPLE 34

2-{(4-Methoxybenezenesulfonyl)-[3-(4-methylaminopiperidin-1-yl)-3-oxo-propyl]amino}hexanoic acid hydroxamide hydrochloride Starting material: (1-{-[(1-hydroxycarbamoylpentyl)-(4-methoxybenzenesulfonyl)-amino]-propionyl}piperidin-4-yl)methyl-carbamic acid tert-butyl ester. MS: 485 (M+1). Analysis calculated for $C_{21}H_{34}N_4O_6S \cdot HCl \cdot 4H_2O$: C, 43.5; H, 7.48; N, 9.67. Found: C, 43.65; H, 7.03; N, 9.79.

EXAMPLE 35

2-{(4-Methoxybenzenesulfonyl)-[3-(4-methylaminopiperidin-1-yl)-3-oxo-proyl]amino}-4,4-dimethylpentanoic acid hydroxyamide hydrochloride Starting material: (1-{3-[(1-hydroxy-carbamoyl-3,3-dimethylbutyl)(4-methoxybenezenesulfonyl) amino]propionyl}piperidin-4-yl)methylcarbamic acid tert-butyl ester. MS: 499 (M+1).

EXAMPLE 36

N-Hydroxy-2-{(4-methoxybenzenesulfonyl)-[3-(4-methylaminopiperidin-1-yl)-3-oxopropyl]amino}-3-phenylpropionamide hydrochloride Starting material: (1-{3-[(1-hydroxycarbamoyl-2-phenylethyl)(4-methoxybenzenesulfonyl)-amino] propionyl}piperidin-4-yl)methylcarbamic acid tert-butyl ester. MS: 519 (M+1).

EXAMPLE 37

3-(4-Fluorophenyl)-N-hydroxy-2-{(4-methoxybenezenesulfonyl)-[3-(4-methylamino piperidin-1-yl)-3-oxo-propyl]amino}propionamide hydrochloride Starting material: (1-{3-[[2-(4-fluorophenyl)-1-hydroxycarbamoylethyl]-(4-methoxybenzenesulfonyl)amino]propionyl}-piperidin-4-yl)methylcarbamic acid tert-butyl ester (Example 21). MS: 537 (M+1). Analysis calculated for $C_{25}H_{33}FN_4O_6S \cdot HCl \cdot 2H_2O$: C, 49.30; H, 6.29; N, 9.20. Found: C, 49.14; H, 5.82; N, 9.24.

EXAMPLE 38

N-Hydroxy-2-{(4-methoxybenzenesulfonyl)-[3-(4-methylaminopiperidin-1-yl)-3-oxopropyl]amino}-4-phenylbutyramide hydrochloride Starting material: (1-{3-[(1-hydroxycarbamoyl-3-phenylpropyl)(4-methoxybenzenesulfonyl) amino] propionyl}piperidin-4-yl)methylcarbamic acid tert-butyl ester. Melting Point 160–170° C. MS: 533 (M+1). Analysis calculated for $C_{26}H_{36}N_4O_6S \cdot HCl \cdot 1.5H_2O$: C, 52.38; H, 6.76; N, 9.40. Found: C, 52.25; H, 6.40; N, 9.00.

EXAMPLE 39

3-tert-Butoxy-N-hydroxy-2-{(4-methoxybenzenesulfonyl)-[3-(4-methyl-amino-piperidin-1-yl)-3-oxopropyl]-amino}propionamide hydrochloride Starting material: (1-{3-[(2-tert-butoxy-1-hydroxycarbamoylethyl)(4-methoxybenzenesulfonyl) amino]propionyl}piperidin-4-yl)methylcarbamic acid tert-butyl ester. MS: 515 (M+1).

EXAMPLE 40

3-Cyclohexyl-N-hydroxy-2-{(4-methoxybenzenesulfonyl)-[3-(4-methyl-amino-piperidin-1-yl)-3-oxopropyl]amino}propionamide hydrochloride Starting material: (1-{3-[(2-cyclohexyl-1-hydroxycarbamoylethyl)-(4-methoxybenzenesulfonyl) amino]propionyl}piperidin-4-yl)methylcarbamic acid tert-butyl ester. MS: 525 (M+1).

EXAMPLE 41

N-Hydroxy-2-{(4-methoxybenzenesulfonyl)-[3-(4-methylaminopiperidin-1-yl)-3-oxopropyl]amino}-3-naphthalen-1-ylpropionamide hydrochloride Starting material: (1-{3-[(1-hydroxy-carbamoyl-2-naphthalen-1-ylethyl)-(4-methoxybenzenesulfonyl) amino]propionyl}-piperidin-4-yl)methylcarbamic acid tert-butyl ester. MS: 569 (M+1).

EXAMPLE 42

1-{3-[(Cyclohexylhydroxycarbamoylmethyl)-(4-methoxybenzenesulfonyl)-amino]-propionyl}piperidine-4-carboxylic acid To a solution of 1-{3-[(cyclohexylhydroxycarbamoylmethyl)(4- methoxybenzenesulfonyl) amino]propionyl}piperidine-4-carboxylic acid ethyl ester (0.62 grams, 1.16 mmol) (Example 17) in ethanol (45 mL) and water (5 mL) was added lithium hydroxide monohydrate (0.24 grams, 5.72 mmol). After stirring for 3 hours at room temperature ethanol-washed Amberlite IR-120 plus ion exchange resin (6 grams) was added. Stirring was continued for 15 minutes and then the mixture was filtered. The filtrate was concentrated in vacuo to give 1-{3-[(cyclohexylhydroxycarbamoylmethyl)-(4-methoxy-benzenesulfonyl)amino]propionyl}-piperidine-4-carboxylic acid monohydrate as a white solid (0.52 grams, 88%). MS: 526 (M+1). Analysis calculated for $C_{24}H_{35}N_3O_8S \cdot H_2O$: C, 53.05; H, 6.86; N, 7.73. Found: C, 53.53; H, 7.15; N, 7.70.

The title compounds of Examples 43–53 were prepared analogously to that described in Example 45 using the starting material indicated.

EXAMPLE 43

1-{3-[(1-Hydroxycarbamoyl-2-methylpropyl)(4-methoxybenzene-sulfonyl)amino] propionyl}piperidine-4-carboxylic acid Starting material: 1-{3-[(1-hydroxycarbamoyl-2-methylpropyl)(4-methoxybenzene-sulfonyl) amino] propionyl}piperidine-4-carboxylic acid ethyl ester. MS: 486 (M+1).

EXAMPLE 44

(4-{3-[(1-Hydroxycarbamoyl-2-methylpropyl)(4-methoxybenzene-sulfonyl)amino] propionyl}piperazin-1-yl)acetic acid Starting material: (4-{3-[(1-hydroxycarbamoyl-2-methylpropyl)(4-methoxybenzene-sulfonyl) amino]-propionyl}piperazin-1-yl)acetic acid ethyl ester (Example 8). MS: 500 (M+1).

EXAMPLE 45

1-{3-[(1-Hydroxycarbamoyl-3-methylbutyl)-(4-methoxybenzenesulfonyl)-amino]-propionyl}piperidine-4-carboxylic acid Starting material: 1-{3-[(1-hydroxycarbamoyl-3-methylbutyl)(4-methoxybenzenesulfonyl)-amino] propionyl}piperidine-4-carboxylic acid ethyl ester. Melting Point 118–120° C. MS: 500 (M+1).

EXAMPLE 46

1-{3-[(1-Hydroxycarbamoylpentyl)(4-methoxybenzenesulfonyl)amino]-propionyl}piperidine-4-carboxylic acid Starting material: 1-{3-[(1-hydroxycarbamoylpentyl)(4-methoxybenzenesulfonyl)-amino]propionyl}piperidine-4-carboxylic acid ethyl ester. MS: 500 (M+1).

EXAMPLE 47

1-{3-[(1-Hydroxycarbamoyl-3,3-dimethylbutyl)(4-methoxy-benzene-sulfonyl)-amino] propionyl}piperidine-4-carboxylic acid Starting material: 1-{3-[(1-hydroxycarbamoyl-3,3-dimethylbutyl)(4-methoxybenzenesulfonyl)-amino] propionyl}piperidine-4-carboxylic acid ethyl ester. MS: 514 (M+1).

EXAMPLE 48

1-{3-[(1-Hydroxycarbamoyl-2-phenylethyl)-(4-methoxybenzenesulfonyl)-amino]-propionyl}piperidine-4-carboxylic acid Starting material: 1-{3-[(1-hydroxycarbamoyl-2-phenylethyl)(4-methoxybenzenesulfonyl)-amino] propionyl}piperidine-4-carboxylic acid ethyl ester. MS 534 (M+1).

EXAMPLE 49

1-{3-[[2-(4-Fluorophenyl)-1-hydroxycarbamoylethyl](4-methoxybenzene-sulfonyl) amino]propionyl}piperidine-4-carboxylic acid Starting material: 1-{3-[[2-(4-fluorophenyl)-1-hydroxycarbamoylethyl](4-methoxybenzenesulfonyl) amino]propionyl}piperidine-4-carboxylic acid ethyl ester. MS: 552 (M+1). Analysis calculated form $C_{25}H_{30}FN_3O_8S \cdot 0.5H_2O$: C, 53.56; H, 5.57; N, 7.50. Found: C, 53.53; H, 5.39; N, 7.28.

EXAMPLE 50

1-{3-[(1-Hydroxycarbamoyl-3-phenylpropyl)(4-methoxybenzenesulfonyl)-amino]-propionyl}piperidine-4-carboxylic acid Starting material: 1-{3-[(1-hydroxycarbamoyl-3-phenyl-propyl)-(4-methoxybenzenesulfonyl)-amino] propionyl}piperidine-4-carboxylic acid ethyl ester. Melting Point 85–92° C. MS: 598 (M+1).

EXAMPLE 51

1-{3-[(2-tert-Butoxy-1-hydroxycarbamoylethyl)(4-methoxybenzene-sulfonyl)-amino] propionyl}piperidine-4-carboxylic acid Starting material: 1-{3-[(2-tert-butoxy-1-hydroxycarbamoylethyl)(4-methoxybenzenesulfonyl)-amino]propionyl}piperidine-4-carboxylic acid ethyl ester. MS: 529 (M+1).

EXAMPLE 52

1-{3-[(2-Cyclohexyl-1-hydroxycarbamoylethyl)(4-methoxybenzene-sulfonyl)-amino] propionyl}piperidine-4-carboxylic acid Starting material: 1-{3-[(2-cyclohexyl-1-hydroxycarbamoylethyl)(4-methoxybenzenesulfonyl) amino]propionyl}piperidine-4-carboxylic acid ethyl ester. MS: 540 (M+1).

EXAMPLE 53

1-{[(1-Hydroxycarbamoyl-2-naphthalen-1-ylethyl) (4-methoxybenzene-sulfonyl) amino] propionyl}piperidine-4-carboxylic acid Starting material: 1-{3-[(1-hydroxycarbamoyl-2-naphthalen-1-ylethyl)(4-methoxybenzenesulfonyl) amino]propionyl}piperidine-4-carboxylic acid ethyl ester. MS: 584 (M+1).

EXAMPLE 54

N-Hydroxy-2-[{3-[4-(2-hydroxyethyl)piperazin-1-yl]-3-oxopropyl}-(4-methoxybenzenesulfonyl) amino]-3-methlbutyramide (A) To a solution of 2-[(2-carboxyethyl)-(4-methoxybenzenesulfonyl)amino]-3-methylbutyric acid benzyl ester(prepared starting from D-valine benzyl ester according to the procedure of Example 1, steps A to D) (1.35 grams, 3.0 mmol) in methylene chloride (45 mL) were added sequentially triethylamine (0.92 mL, 6.9 mmol), 2-piperazin-1-ylethanol (0.43 grams, 3.3 mmol) and (benzotriazol-1-yloxy)tris(dimethylamino)-phosphonium hexafluoroborate (1.53 grams, 3.45 mmol). The resulting mixture was stirred for 16 hours at room temperature and then concentrated in vacuo. The residue was taken up in ethyl acetate and washed with saturated sodium bicarbonate solution and brine. The solution was dried over magnesium sulfate and concentrated to yield and oil which was chromatographed on silica gel eluting with 5% methanol in chloroform to afford 2-[{3-[4-(2-hydroxyethyl)piperazin-1-yl]-3-oxopropyl}(4-methoxybenzenesulfonyl)amino]-3-methylbutyric acid benzyl esteras an oil (1.40 grams, 83%). Conversion to the hydrochloride salt was subsequently carried out using anhydrous hydrochloric acid in cold (0° C.) methylene chloride.

(B) To a solution of 2-[{3-[4-(2-hydroxyethyl)piperazin-1-yl]-3-oxopropyl}(4-methoxybenzenesulfonyl)amino]-3-methylbutyric acid benzyl ester hydrochloride (1.49 grams, 2.49 mmol) in ethanol (80 mL) was added 10% palladium on activated carbon (0.11 grams). The mixture was agitated under 3 atmospheres hydrogen in a Parr shaker for 16 hours. The catalyst was removed by filtration through nylon (pore size 0.45 $\mu$m) and the solvent was evaporated leaving 2-[{3-[4-(2-hydroxyethyl)piperazin-1-yl]-3-oxo-propyl}(4-methoxybenzenesulfonyl)amino]-3-methylbutyric acid hydrochloride as a white solid (1.6 grams, 92%).

(C) To a solution of 2-[{3-[4-(2-hydroxyethyl)piperazin-1-yl]-3-oxopropyl}(4-methoxy-benzenesulfonyl)amino]-3-methylbutyric acid hydrochloride (1.10 grams, 2.17 mmol) in methylene chloride (50 mL) and N,N-dimethylformamide (0.5 mL) were added sequentially O-benzylhydroxylamine hydrochloride (0.41 grams, 2.60 mmol), triethylamine (0.91 mL, 6.5 mmol) and (benzotriazol-1-yloxy)tris-(dimethylamino)-phosphonium hexafluoroborate (1.20 grams, 2.71 mmol). The resulting mixture was stirred for 16 hours at room temperature and then concentrated in vacuo. The residue was taken up in ethyl acetate and washed successively with saturated sodium bicarbonate solution, water and brine. The solution was dried over magnesium sulfate and concentrated to yield an oil which was chromatographed on silica gel eluting with 3% methanol in chloroform to afford N-benzyloxy-2-[{3-[4-(2-hydroxyethyl)piperazin-1-yl]-3-oxopropyl}(4-methoxybenzenesulfonyl)amino]-3-methylbutyramide as a clear oil (0.85 grams, 68%). Conversion to the hydrochloride salt was subsequently carried out using anhydrous hydrochloric acid in cold (0° C.) methylene chloride.

(D) To a solution of N-benzyloxy-2-[{3-[4-(2-hydroxyethyl)piperazin-1-yl]-3-oxopropyl}-(4-methoxybenzenesulfonyl)amino]-3-methylbutyramide hydrochloride (0.39 grams, 0.63 mmol) in methanol (30 mL) was added 5% palladium on barium sulfate (0.19 grams). The mixture was agitated under 3 atmospheres hydrogen in a Parr shaker for 2.25 hours. The catalyst was removed by filtration through nylon (pore size 0.45 $\mu$m) and the solvent was evaporated to a tan foam which was chromatographed on silica gel eluting with 15% methanol in chloroform containing 0.5% ammonium hydroxide. Clean fractions containing the desired product were taken up in saturated sodium bicarbonate solution. The resulting mixture was extracted several times with ethyl acetate and the combined extracts were concentrated to afford N-hydroxy-2-[{3-[4-(2-hydroxyethyl)piperazin-1-yl]-3-oxopropyl}-(4-methoxybenzenesulfonyl)amino]-3-methyl-butyramide as an oil. The hydrochloride salt (0.20 grams, 61%) was formed using anhydrous hydrochloric acid in cold (0° C.) methanol. MS: 487 (M+1). Analysis calculated for $C_{21}H_{34}N_4O_7S \bullet HCl \bullet 0.5H_2O$: C, 47.41; H, 6.82; N, 10.53. Found: C, 47.41; H, 7.11; N, 9.91.

The title compounds of Examples 55–57 were prepared analogously to that described in Example 58 using the indicated amine in step A.

EXAMPLE 55

2-[[3-(4-Dimethylaminopiperidin-1-yl)-3-oxopropyl] (4-methoxybenzene-sulfonyl)amino]-N-hydroxy-3-methylbutyramide Coupled with dimethylpiperidin-4-ylamine. MS: 485 (M+1).

EXAMPLE 56

N-Hydroxy-2-[{3-[4-(3-hydroxypropyl)piperazin-1-yl]-3-oxopropyl}-(4-methoxy-benzenesulfonyl) amino]-3-methylbutyramide Coupled with 3-piperazin-1-ylpropan-1-ol. MS: 500 (M+1).

EXAMPLE 57

2-[(3-[1,4']Bipiperidinyl-1'-yl-3-oxopropyl)-(4-methoxybenzenesulfonyl)-amino]-N-hydroxy-3-methylbutyramide Coupled with using [1,4']bipiperidinyl. MS: 525 (M+1). Analysis calculated for $C_{25}H_{40}N_4O_6S \bullet HCl \bullet 1.5H_2O$: C, 51.05; H, 7.54; N, 9.52. Found: C, 50.80; H, 7.45; N, 9.36.

EXAMPLE 58

1-{3-[(1-Hydroxycarbamoyl-2-methylpropyl)-(4-phenoxybenzenesulfonyl)amino]propionyl] piperidine-4-carboxylic Acid Ethyl Ester The title compound was prepared analogously to that described in Example 1 using D-valine benzyl ester and 4-phenoxybenzenesulfonyl chloride as the starting materials in step A and piperidine-4-carboxylic acid ethyl ester in step E. Analysis calculated for $C_{28}H_{37}N_3O_8S \cdot 0.1CH_2Cl_2$: C, 57.78; H, 6.42; N, 7.19. Found: C, 57.46; H, 6.41; N, 7.11.

EXAMPLE 59

1-{3-[(1-Hydroxycarbamoyl-2-methylpropyl)-(4-phenoxybenzenesulfonyl)amino]propionyl] piperidine-4-carboxylic Acid The title compound was prepared analogously to that described in Example 42 using 1-{3-[(1-hydroxycarbamoyl-2-methylpropyl)-(4-phenoxybenzenesulfonyl)amino] propionyl]piperidine-4-carboxylic acid ethyl ester (Example 58) as the starting material. MS: 548 (M+1). Analysis calculated for $C_{26}H_{33}N_3O_8S \cdot 0.5H_2O$: C, 56.10; H, 6.16; N, 7.75. Found: C, 55.99; H, 6.06; N, 7.43.

What is claimed is:

1. A compound of the formula

[Structure I: HO-NH-C(=O)-C(R³)(R⁴)-N(SO₂Q)-(CH₂)ₙ-C(=O)-X]

or the pharmaceutically acceptable salts thereof, wherein
n is 1 to 6;
X is $OR^1$ wherein $R^1$ is as defined below; azetidinyl, pyrrolidinyl, piperidinyl, morpholinyl, thiomorpholinyl, indolinyl, isoindolinyl, tetrahydroquinolinyl, tetrahydroisoquinolinyl, piperazinyl or a bridged diazabicycloalkyl ring selected from the group consisting of a
[Structure a: piperazine ring with N-CH₃, (CH₂)ₘ, (CH₂)ᵣ, N-H]

b
[Structure b: piperazine ring with N-CH₃, (CH₂)ᵣ, (CH₂)ₘ, N-H]

c
[Structure c: bridged ring with N-CH₃, (CH₂)ᵣ, N-H]

d
[Structure d: bridged ring with N-CH₃, (CH₂)ᵣ, (CH₂)ₚ, N]

e
[Structure e: bicyclic ring with N-CH₃, (CH₂)ᵣ, N]

wherein
r is 1, 2 or 3;
m is 1 or 2; and
p is 0 or 1;
wherein each heterocyclic group may optionally be substituted by one or two groups selected from hydroxy, $(C_1-C_6)$ alkyl, $(C_1-C_6)$alkoxy, $(C_1-C_{10})$acyl, $(C_1-C_{10})$acyloxy, $(C_6-C_{10})$aryl, $(C_5-C_9)$heteroaryl, $(C_6-C_{10})$aryl$(C_1-C_6)$alkyl, $C_5-C_9$)heteroaryl $(C_1-C_6)$alkyl, hydroxy $(C_1-C_6)$ alkyl, $(C_1-C_6)$alkoxy $(C_1-C_6)$alkyl, $(C_1-C_6)$acyloxy $(C_1-C_6)$alkyl, $(C_1-C_6)$alkylthio, $(C_1-C_6)$alkylthio $(C_1-C_6)$ alkyl, $(C_6-C_{10})$arylthio, $(C_6-C_{10})$arylthio$(C_1-C_6)$alkyl, $R^9R^{10}N$, $R^9R^{10}NSO_2$, $R^9R^{10}NCO$, $R^9R^{10}NCO(C_1-C_6)$alkyl wherein $R^9$ and $R^{10}$ are each independently hydrogen, $(C_1-C_6)$alkyl, $(C_6-C_{10})$aryl, $C_5-C_9$)heteroaryl, $(C_6-C_{10})$ aryl $(C_1-C_6)$alkyl or $(C_5-C_9)$heteroaryl $(C_1-C_6)$alkyl or $R^9$ and $R^{10}$ may be taken together with the nitrogen to which they are attached to form an azetidinyl, pyrrolidinyl, piperidinyl, morpholinyl or thiomorpolinyl ring; $R^{12}SO_2$, $R^{12}SO_2NH$ wherein $R^{12}$ is trifluoromethyl, $(C_1-C_6)$alkyl, $(C_6-C_{10})$aryl, $(C_5-C_9)$heteroaryl, $(C_6-C_{10})$aryl$(C_1-C_6)$alkyl or $(C_5-C_9)$heteroaryl $(C_1-C_6)$alkyl; $R^{13}CONR^9$ wherein $R^9$ is as defined above and $R^{13}$ is hydrogen, $(C_1-C_6)$alkyl, $(C_1-C_6)$alkoxy, $(C_6-C_{10})$aryl, $(C_5-C_9)$heteroaryl, $(C_1-C_6)$ aryl$(C_1-C_6)$alkyl$(C_6-C_{10})$aryl$(C_1-C_6)$alkoxy or $(C_5-C_9)$ heteroaryl$(C_1-C_6)$alkyl; $R^{14}OOC$, $R^{14}OOC(C_1-C_6)$alkyl wherein $R^{14}$ is $(C_1-C_6)$alkyl, $(C_6-C_{10})$aryl, $(C_5-C_9)$ heteroaryl, $(C_6-C_{10})$aryl $(C_1-C_6)$alkyl, 5-indanyl, $CHR^5OCOR^6$ wherein $R^5$ is hydrogen or $(C_1-C_6)$alkyl and $R^6$ is $(C_1-C_6)$alkyl, $(C_1-C_6)$alkoxy or $(C_6-C_{10})$aryl; $CH_2CONR^7R^8$ wherein $R^7$ and $R^8$ are each independently hydrogen or $(C_1-C_6)$alkyl or may be taken together with the nitrogen to which they are attached to form an azetidinyl, pyrrolidinyl, piperidinyl, morpholinyl or thiomorpholinyl ring; or $R^{15}O$ $(C_1C_6)$alkyl wherein $R^{15}$ is $H_2N(CHR^{16})CO$ wherein $R^{16}$ is the side chain of a natural D- or L-amino acid;

$R^1$ is $(C_6-C_{10})$aryl, $(C_5-C_9)$heteroaryl, $(C_6-C_{10})$aryl $(C_1-C_6)$alkyl, 5-indanyl, $CHR^5OCOR^6$ or $CH_2CONR^7R^8$ wherein $R^5$, $R^6$, $R^7$ and $R^8$ are as defined above;

$R^3$ and $R^4$ are each independently selected from the group consisting of hydrogen, $(C_1-C_6)$alkyl, trifluoromethyl, trifluoromethyl$(C_1-C_6)$alkyl, $(C_1-C_6)$alkyl (difluoromethylene), $(C_1-C_3)$alkyl(difluoromethylene) $(C_1-C_3)$alkyl, $(C_6-C_{10})$aryl, $(C_5-C_9)$heteroaryl, $(C_6-C_{10})$aryl$(C_1-C_6)$alkyl, $(C_5-C_9)$heteroaryl$(C_1-C_6)$ alkyl, $(C_6-C_{10})$aryl$(C_6-C_{10})$aryl, $(C_6-C_{10})$aryl $(C_6-C_{10})$aryl$(C_1-C_6)$alkyl, $C_3-C_6$)cycloalkyl, $(C_3-C_6)$ cycloalkyl$(C_1-C_6)$alkyl, hydroxy$(C_1-C_6)$alkyl, $C_1-C_{10}$)acyloxy$(C_1-C_6)$alkyl, $(C_1-C_6)$alkoxy$(C_1-C_6)$ alkyl, $(C_1-C_{10})$acylamino$(C_1-C_6)$alkyl, piperidyl, $(C_1-C_6)$alkylpiperidyl, $(C_6-C_{10})$aryl$(C_1-C_6)$alkoxy $(C_1-C_6)$alkyl, $(C_5-C_9)$heteroaryl$(C_1-C_6)$alkoxy $(C_1-C_6)$alkyl, $(C_1-C_6)$alkylthio$(C_1-C_6)$alkyl, $(C_6-C_{10})$ arylthio$(C_1-C_6)$alkyl, $(C_1-C_6)$alkylsulfinyl$(C_1-C_6)$ alkyl, $(C_6-C_{10})$arylsulfinyl$(C_1-C_6)$alkyl, $(C_1-C_6)$ alkylsulfonyl$(C_1-C_6)$alkyl, $(C_6-C_{10})$arylsulfonyl $(C_1-C_6)$alkyl, amino$(C_1-C_6)$alkyl, $(C_1-C_6)$alkylamino $(C_1-C_6)$alkyl, $((C_1-C_6)$alkylamino$_2(C_1-C_6)$alkyl, $R^{17}CO(C_1-C_6)$alkyl wherein $R^{17}$is $R^{14}O$ or $R^7R^8N$ wherein $R^7$, $R^8$ and $R^{14}$ are as defined above; or $R^{18}(C_1-C_6)$alkyl wherein $R^{18}$ is piperazinyl, $(C_1-C_{10})$ acylpiperazinyl, $(C_6-C_{10})$arylpiperazinyl, $(C_5-C_9)$ heteroarylpiperazinyl, $(C_1-C_6)$alkylpiperazinyl, $(C_6-C_{10})$aryl$(C_1-C_6)$alkylpiperazinyl, $(C_5-C_9)$ heteroaryl$(C_1-C_6)$alkylpiperazinyl, morpholinyl, thiomorpholinyl, piperidinyl, pyrrolidinyl, piperidyl, $(C_1-C_6)$alkylpiperidyl, $(C_6-C_{10})$arylpiperidyl, $(C_5-C_9)$ heteroarylpiperidyl, $(C_6-C_{10})$aryl$(C_1-C_6)$ alkylpiperidyl, $(C_5-C_9)$heteroaryl$(C_1-C_6)$ alkylpiperidyl or $(C_1-C_{10})$acylpiperidyl;

or $R^3$ and $R^4$ may be taken together to form a $(C_3-C_6)$ cycloalkyl, oxacyclohexyl, thiocyclohexyl, indanyl or tetralinyl ring or a group of the formula $$\begin{array}{c} \\ N \\ | \\ R^{21} \end{array}$$

wherein $R^{21}$ is hydrogen, $(C_1-C_{10})$acyl, $(C_1-C_6)$alkyl, $(C_6-C_{10})$aryl$(C_1-C_6)$alkyl, $(C_5-C_9)$heteroaryl$(C_1-C_6)$alkyl or $(C_1-C_6)$alkylsulfonyl; and Q is $(C_1-C_6)$alkyl, $(C_6-C_{10})$aryl, $(C_6-C_{10})$aryloxy $(C_6-C_{10})$aryl, $(C_6-C_{10})$aryl$(C_6-C_{10})$aryl, $(C_6-C_{10})$aryl $(C_6-C_{10})$aryl$(C_1-C_6)$alkyl, $(C_6-C_{10})$aryloxy$(C_5-C_9)$ heteroaryl, $(C_5-C_9)$heteroaryl, $(C_1-C_6)$alkyl$(C_6-C_{10})$ aryl, $(C_1-C_6)$alkoxy$(C_6-C_{10})$aryl, $(C_6-C_{10})$aryl $(C_1-C_6)$alkoxy$(C_6-C_{10})$aryl, $(C_6-C_{10})$aryl$(C_1-C_6)$ alkoxy$(C_1-C_6)$alkyl, $(C_5-C_9)$heteroaryloxy$(C_6-C_{10})$ aryl, $(C_1-C_6)$alkyl$(C_5-C_9)$heteroaryl, $(C_1-C_6)$alkoxy $(C_5-C_9)$heteroaryl, $(C_6-C_{10})$aryl$(C_1-C_6)$alkoxy $(C_5-C_9)$heteroaryl, $(C_5-C_9)$heteroaryloxy$(C_5-C_9)$ heteroaryl, $(C_6-C_{10})$aryloxy$(C_1-C_6)$alkyl, $(C_5-C_9)$ heteroaryloxy$(C_1-C_6)$alkyl, $(C_1-C_6)$alkyl$(C_6-C_{10})$ aryloxy$(C_6-C_{10})$aryl, $(C_1-C_6)$alkyl$(C_5-C_9)$ heteroaryloxy$(C_6-C_{10})$aryl, $(C_1-C_6)$alkyl$(C_6-C_{10})$ aryloxy$(C_5-C_9)$heteroaryl, $(C_1-C_6)$alkoxy$(C_6-C_{10})$ aryloxy$(C_6-C_{10})$aryl, $(C_1-C_6)$alkoxy$(C_5-C_9)$ heteroaryloxy$(C_6-C_{10})$aryl or $(C_1-C_6)$alkoxy$(C_6-C_{10})$ aryloxy$(C_5-C_9)$heteroaryl wherein each aryl group is optionally substituted by fluoro, chloro, bromo, $(C_1-C_6)$alkyl, $(C_1-C_6)$alkoxy or perfluoro$(C_1-C_3)$ alkyl;

with the proviso that X must be substituted when defined as azetidinyl, pyrrolidinyl, morpholinyl, thiomorpholinyl, indolinyl, isoindolinyl, tetrahydroquinolinyl, tetrahydroisoquinolinyl, piperazinyl, $(C_1-C_{10})$acylpiperazinyl, $(C_1-C_6)$ alkylpiperazinyl, $(C_6-C_{10})$arylpiperazinyl, $(C_5-C_9)$ heteroarylpiperazinyl or a bridged diazabicycloalkyl ring.

2. A compound according to claim 1, wherein n is 2.

3. A compound according to claim 1, wherein either $R^3$ or $R^4$ is not hydrogen.

4. A compound according to claim 1, wherein Q is $(C_1-C_6)$alkoxy$(C_6-C_{10})$aryl, $(C_6-C_{10})$aryl$(C_1-C_6)$alkoxy $(C_6-C_{10})$aryl, phenoxy$(C_6-C_{10})$aryl, 4-fluorophenoxy $(C_6-C_{10})$aryl, 4-fluorobenzyloxy$(C_6-C_{10})$aryl or $(C_1-C_6)$ alkyl$(C_6-C_{10})$aryloxy$(C_6-C_{10})$aryl.

5. A compound according to claim 1, wherein X is indolinyl or piperidinyl, wherein said indolinyl and piperidinyl are substituted.

6. A compound according to claim 1, wherein n is 2; either $R^3$ or $R^4$ is not hydrogen; Q is $(C_1-C_6)$alkoxy$(C_6-C_{10})$aryl, $(C_6-C_{10})$aryl$(C_1-C_6)$alkoxy$(C_6-C_{10})$aryl, 4-fluorophenoxy $(C_6-C_{10})$aryl, phenoxy$(C_6-C_{10})$aryl, 4-fluorobenzyloxy $(C_6-C_{10})$aryl or $(C_1-C_6)$alkyl$(C_6-C_{10})$aryloxy$(C_6-C_{10})$aryl; and X is indolinyl or piperidinyl, wherein said indolinyl and piperidinyl are substituted.

7. A compound according to claim 1, wherein said compound is selected from the group consisting of:

3-[(Cyclohexylhydroxycarbamoylmethyl)-(4-methoxybenzenesulfonyl)-amino]-propionic acid indan-5-yl ester;

Acetic acid 1-{3-[(1-hydroxycarbamoyl-2-methylpropyl)-(4-methoxy-benzenesulfonyl)-amino] propionyl}piperidin-4-yl ester;

2-Cyclohexyl-N-hydroxy-2-[[3-(4-hydroxypiperidin-1-yl)-3-oxopropyl]-(4-methoxy-benzenesulfonyl)amino] acetamide;

Benzoic acid 1-{3-[(1-hydroxycarbamoyl-2-methylpropyl)-(4-methoxy-benzenesulfonyl)amino] propionyl}piperidin-4-yl ester;

N-Hydroxy-2-[[3-(4-hydroxypiperidin-1-yl)-3-oxopropyl]-(4-methoxy-benzenesulfonyl)amino]-3-methylbutyramide;

1-{3-[(Cyclohexylhydroxycarbamoylmethyl)-4-methoxybenzenesulfonyl)-amino] propionyl}piperidine-4-carboxylic acid;

1-{3-[(Cyclohexylhydroxycarbamoylmethyl)-(4-methoxybenzenesulfonyl)-amino] propionyl}piperidine-4-carboxylic acid ethyl ester;

2-Cyclohexyl-N-hydroxy-2-{(4-methoxybenzenesulfonyl)-[3-(4-methyl-aminopiperidin-1-yl)-3-oxopropyl]amino}acetamide;

3-(4-Chlorophenyl)-N-hydroxy-2-{(4-methoxybenzenesulfonyl)-[3-(4-methylaminopiperidin-1-yl)-3-oxopropyl] amino}propionamide;

3-Cyclohexyl-N-hydroxy-2-{(4-methoxybenzenesulfonyl)-[3-(4-methyl-aminopiperidin-1-yl)-3-oxopropyl] amino}propionamide;

N-Hydroxy-2-[{3-[4-(2-hydroxy-2-methylpropyl) piperazin-1-yl]-3-oxopropyl}-(4-methoxy-benzenesulfonyl)amino]-3-methylbutyramide;

2,2-Dimethylpropionic acid 2-(4-{3-[(1-hydroxycarbamoyl-2-methylpropyl)-(4-methoxy-benzenesulfonyl)amino]propionyl}piperazin-1-yl) ethyl ester;

Benzoic acid 2-(4-{3-[(1-hydroxycarbamoyl-2-methylpropyl)-(4-methoxybenzenesulfonyl)-amino] propionyl}piperazin-1-yl)-ethyl ester;

2-Cyclohexyl-N-hydroxy-2-[{3-[4-(2-hydroxyethyl) piperazin-1yl]-3-oxopropyl}-(4-methoxybenzenesulfonyl)amino]acetamide;

2-Hydroxy-2-[{3-[5-(2-hydroxyethyl)-2,5-diazabicyclo [2.2.1]-hept-2-yl]-3-oxopropyl}-(4-methoxybenzenesulfonyl)amino]-3-methylbutyramide;

2-}(4-Benzyloxybenzenesulfonyl)-[3-(4-hydroxypiperidin-1-yl)-3-oxopropyl]amino}-N-hydroxy-3-methylbutyramide;

2-Cyclohexyl-2-{[4-(4-fluorophenoxy)benzenesulfonyl]-[3-(4-hydroxypiperidin-1-yl)-3-oxopropyl]-amino}-N-hydroxyacetamide;

2-{[4-(4-Butylphenoxy)benzenesulfonyl]-[3-(4-hydroxypiperidin-1-yl)-3-oxopropyl]-amino}-N-hydroxy-3-methylbutyramide;

1-{(4-Methoxybenzenesulfonyl)-[3-(4-methylaminopiperidin-1-yl)-3-oxopropyl]amino}-cyclopentanecarboxylic acid hydroxyamide;

4-{3-[(1-Hydroxycarbamoyl-2-methylpropyl)-(4-methoxybenzenesulfonyl)amino]-propionyl}piperazine-2-carboxylic acid ethyl ester;

3-[(Cyclohexylhydroxycarbamoylmethyl)-(4-methoxybenzenesulfonyl)amino]propionic acid ethoxycarbonyloxymethyl ester;

3-[(1-Hydroxycarbamoylpentyl)-(4-methoxybenzenesulfonyl)amino]propionic acid ethoxycarbonyloxymethyl ester;

1-{3-[(1-Hydroxycarbamoyl-2-methylpropyl)-(4-phenoxybenzenesulfonyl)amino]propionyl]piperidine-4-carboxylic acid, 3-[[4-(4-Fluorobenzyloxy)-benzenesulfonyl]-(1-hydroxycarbamoyl-2-methyl-propyl)-amino]-propionic acid ethoxycarbonyloxymethyl ester; and 3-[[4-(4-Fluorophenoxy)-benzenesulfonyl]-(1-hydroxycarbamoyl-2-methyl-propyl)-amino]-propionic acid ethoxycarbonyloxymethyl ester.

8. A pharmaceutical composition for (a) the treatment of a condition selected from the group consisting of arthritis, cancer, tissue ulceration, muscular degeneration, restenosis, periodontal disease, epidermolysis bullosa, scleritis, in combination with standard NSAID's and analgesics and in combination with cytotoxic anticancer agents, and other diseases characterized by matrix metalloproteinase activity, AIDS, sepsis, septic shock and other diseases involving the production of tumor necrosis factor (TNF) or (b) the inhibition of matrix metalloproteinases or the production of tumor necrosis factor (TNF) in a mammal, including a human, comprising an amount of a compound of claim 1 effective in such treatment and a pharmaceutically acceptable carrier.

9. A method for the inhibition of (a) matrix metalloproteinases or (b) the production of tumor necrosis factor (TNF) in a mammal, including a human, comprising administering to said mammal an effective amount of a compound of claim 1.

10. A method for treating a condition selected from the group consisting of arthritis, cancer, tissue ulceration, macular degeneration, restenosis, periodontal disease, epidermolysis bullosa, scleritis, compounds of formula I may be used in combination with standard NSAID'S and analgesics and in combination with cytotoxic anticancer agents, and other diseases characterized by matrix metalloproteinase activity, AIDS, sepsis, septic shock and other diseases involving the production of tumor necrosis factor (TNF) in a mammal, including a human, comprising administering to said mammal an amount of a compound of claim 1, effective in treating such a condition.

* * * * *